United States Patent
Kolesnick et al.

(10) Patent No.: US 10,052,387 B2
(45) Date of Patent: Aug. 21, 2018

(54) CERAMIDE REVERSAL OF MULTI-DRUG RESISTANCE

(71) Applicants: Memorial Sloan-Kettering Cancer Center, New York, NY (US); Yissum Research Development Company of the Hebrew University LTD, Jerusalem (IL)

(72) Inventors: Richard Kolesnick, New York, NY (US); Yechezkel Barenholz, Jerusalem (IL); Erez Koren, Ramat Hasharon (IL)

(73) Assignees: MEMORIAL SLOAN-KETTERING CANCER CENTER, New York, NY (US); Yissum Research Development Company of the Hebrew University LTD, Jerusalem (IL)

( * ) Notice: Subject to any disclaimer, the term of this patent is extended or adjusted under 35 U.S.C. 154(b) by 100 days.

(21) Appl. No.: 14/854,891

(22) Filed: Sep. 15, 2015

(65) Prior Publication Data
US 2016/0184433 A1    Jun. 30, 2016

Related U.S. Application Data

(63) Continuation-in-part of application No. PCT/US2014/028828, filed on Mar. 14, 2014.
(Continued)

(51) Int. Cl.
| | |
|---|---|
| *A61K 47/18* | (2017.01) |
| *A61K 47/24* | (2006.01) |
| *A61K 9/107* | (2006.01) |
| *A61K 9/127* | (2006.01) |
| *A61K 31/704* | (2006.01) |

(52) U.S. Cl.
CPC ............ *A61K 47/18* (2013.01); *A61K 9/1075* (2013.01); *A61K 9/1272* (2013.01); *A61K 31/704* (2013.01); *A61K 47/24* (2013.01)

(58) Field of Classification Search
CPC ..................................................... A61K 47/18
See application file for complete search history.

(56) References Cited

U.S. PATENT DOCUMENTS 4,898,735 A    2/1990    Barenholz et al.

FOREIGN PATENT DOCUMENTS

| WO | 2004/096140 A2 | 11/2004 |
| WO | 2006/051549 A2 | 5/2006 |

(Continued)

OTHER PUBLICATIONS

Huang et al, Apoptotic Sphingolipid Ceramide in Cancer Therapy, Journal of Lipids, vol. 2011, Article ID 565316, 15 pages, 2011.*

(Continued)

*Primary Examiner* — Benjamin Packard
(74) *Attorney, Agent, or Firm* — Heslin Rothenberg Farley and Mesiti, PC; Kathy Smith Dias

(57) ABSTRACT

Based on the observation that the application of small amounts of exogenous acid sphingomyelinase to generate endogenous ceramide, or provision of exogenous long-chain natural C16-ceramide resulted in rapid translocation of vacuolar daunorubicin into the nucleus in multi-drug resistant (MDR) cells, the present invention relates to a nano-liposomal preparation that includes C16-ceramide. Exposure of MDR cells to the C16:0 ceramide-based nanoliposomes provide a mechanism to reverse MDR in chemoresistant cells and tumors, by inducing rapid translocation of chemotherapeutic agent from cytoplasmic vesicles to the nucleus.

19 Claims, 28 Drawing Sheets

Related U.S. Application Data

(60) Provisional application No. 61/794,584, filed on Mar. 15, 2013.

(56) References Cited

FOREIGN PATENT DOCUMENTS

| WO | 2009/138806 | A1 | 11/2009 |
|---|---|---|---|
| WO | 2010/030381 | A1 | 3/2010 |
| WO | 2012/125486 | A1 | 9/2012 |
| WO | 2012/154942 | A2 | 11/2012 |

OTHER PUBLICATIONS

Khazanov et al, Langmuir 2008, 24, 6965-6980.*
Veldman, Robert, J., et al., "Inhibition of P-Glycoprotein Activity and Chemosensitization of Multidrug-Resistant Ovarian Carcinoma 2780AD Cells by Hexanoylglucosylceramide", *Biochemical and Biophysical Research Communications*, vol. 266(2), pp. 492-496 (1999).
Ryland Lindsay K., et al., "C6-Ceramide Nanoliposomes Target the Warburg Effect in Chronic Lymphocytic Leukemia", *PLOS ONE*, vol. 8(12), pp. 1-15 (2013).
Avnir, Yuval, et al., "Fabrication Principles and Their Contribution to the Superior in Vivo Therapeutic Efficacy of Nano-Liposomes Remote Loaded with Glucocorticoids", *PLOS ONE*, vol. 6(10), pp. 1-13 (2011).
Allen, Theresa M., et al, "Liposomal Drug Delivery Systems: From Concept to Clinical Applications", *Advanced Drug Delivery Reviews*, vol. 65, pp. 36-48 (2013).
Medler, Terry, R., et al. "Apoptotic Sphingolipid Signaling by Ceramides in Lung Endothelial Cells", *American Journal of Respiratory Cell and Molecular Biology*, vol. 38, pp. 639-646 (2008).
International Search Report for PCT/US2014/028828 dated Jun. 8, 2014.

\* cited by examiner

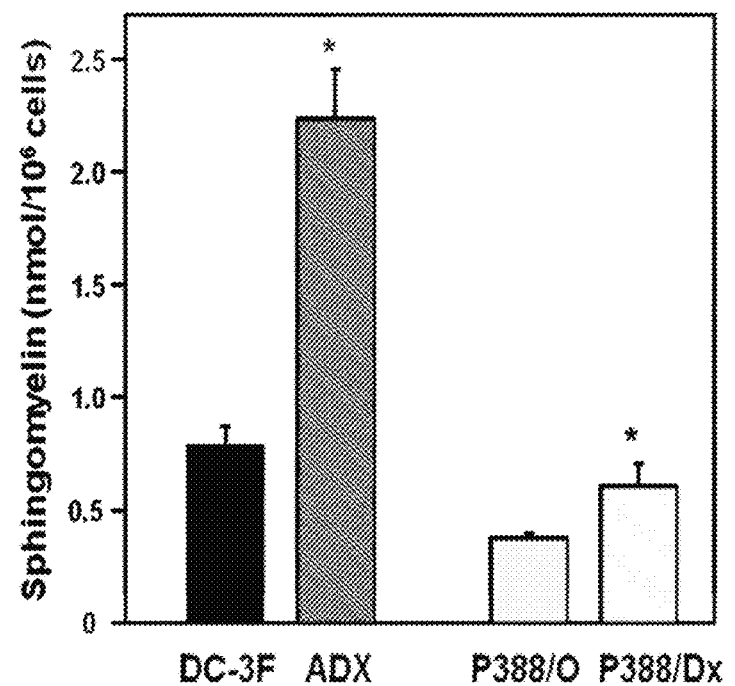
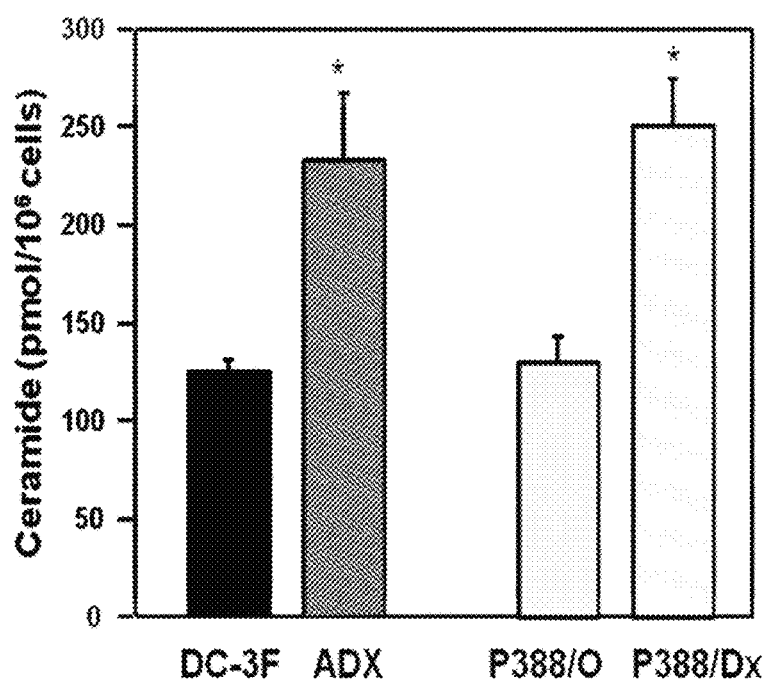
FIGURE 2

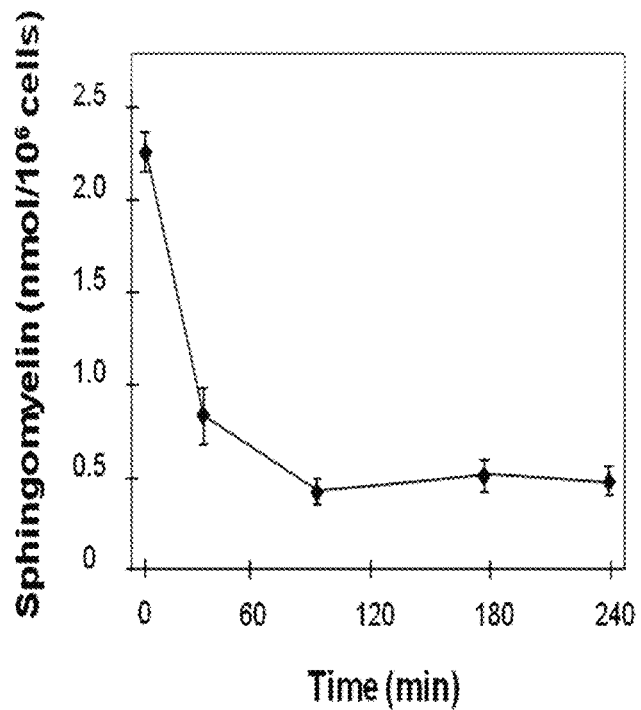
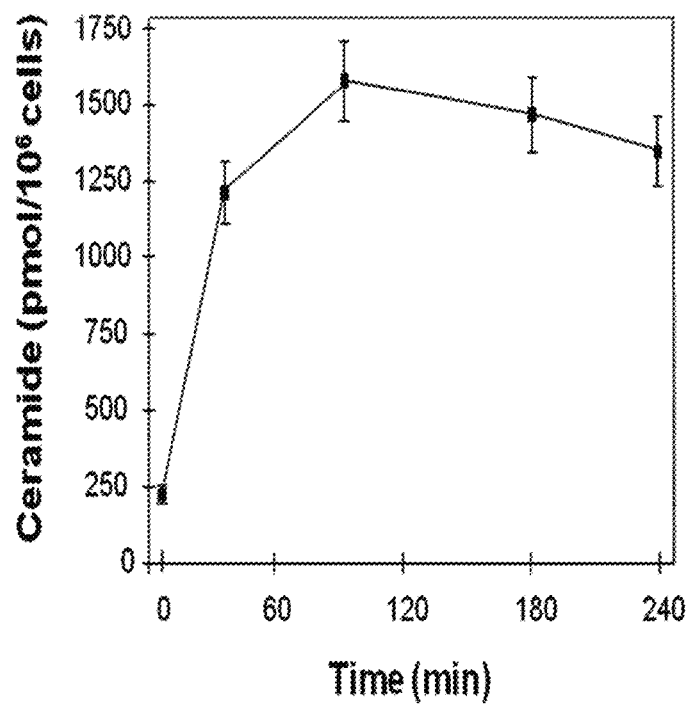
FIGURE 3

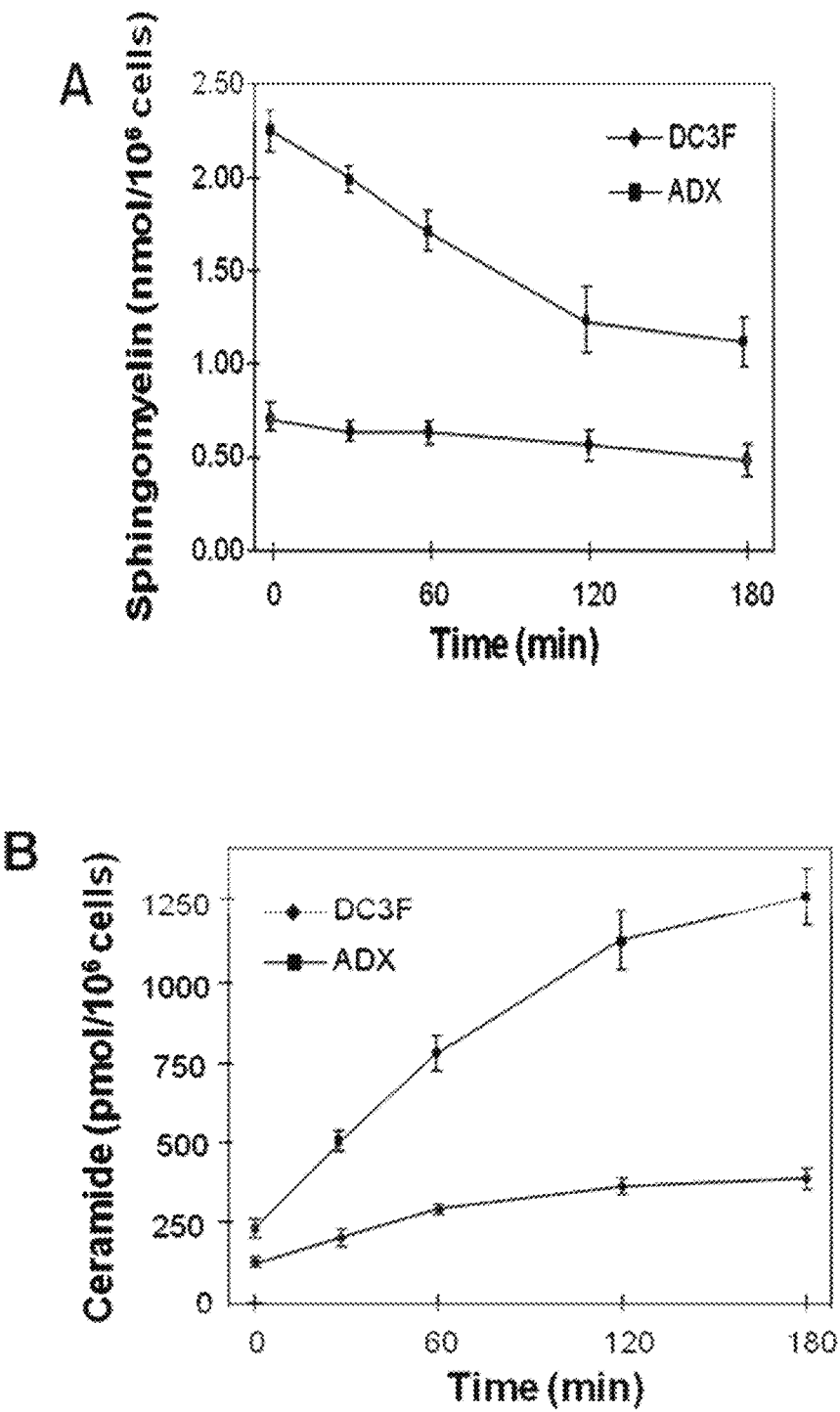
FIGURE 4A-B

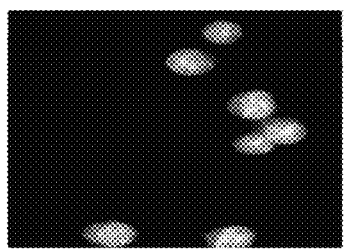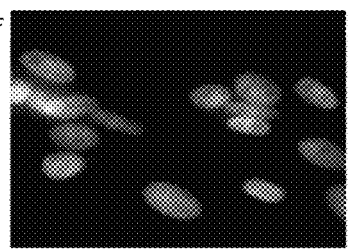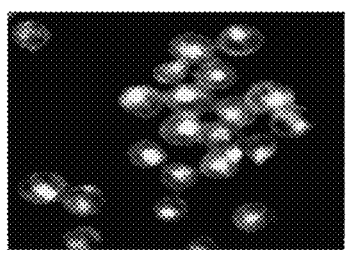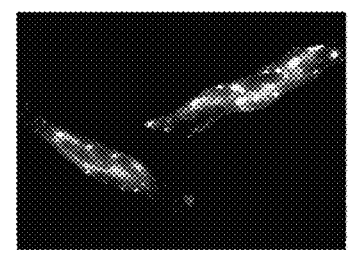
FIGURE 5

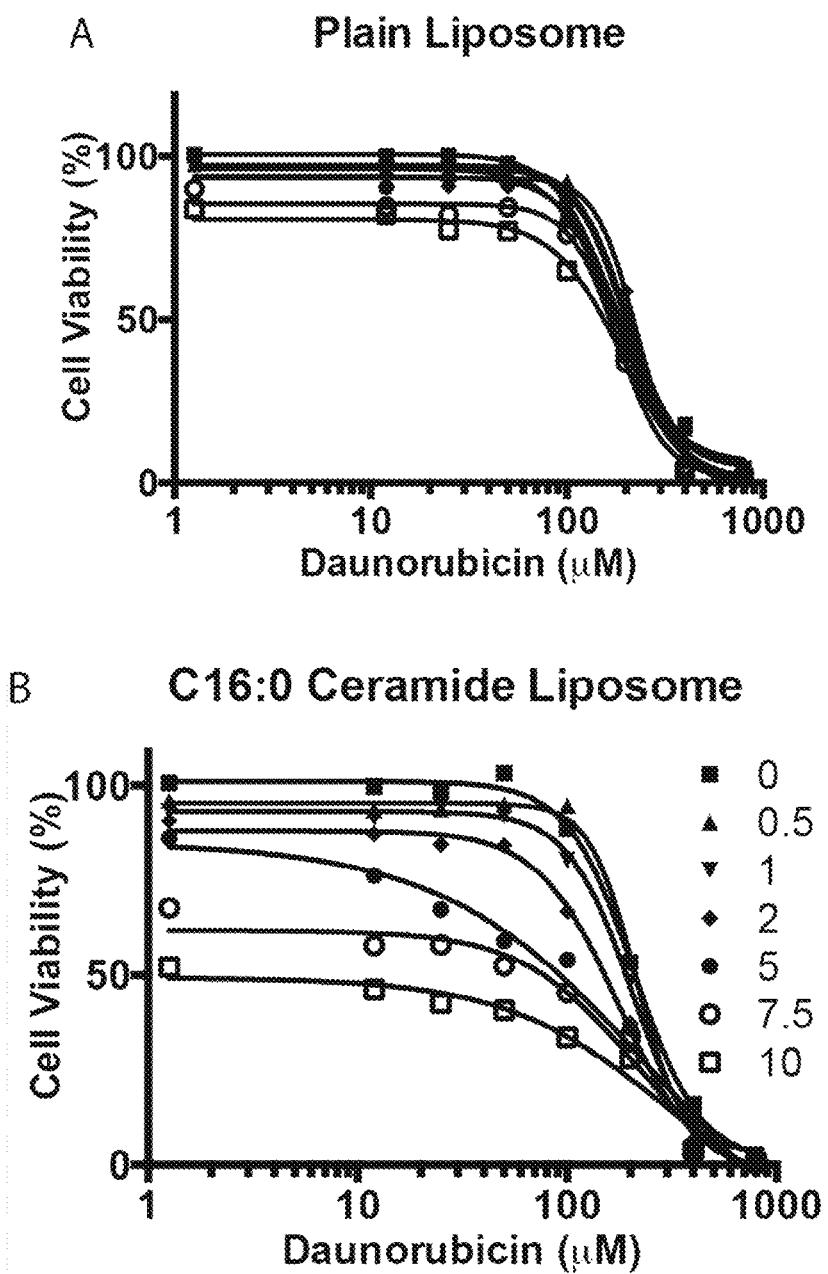
FIGURE 16A-B

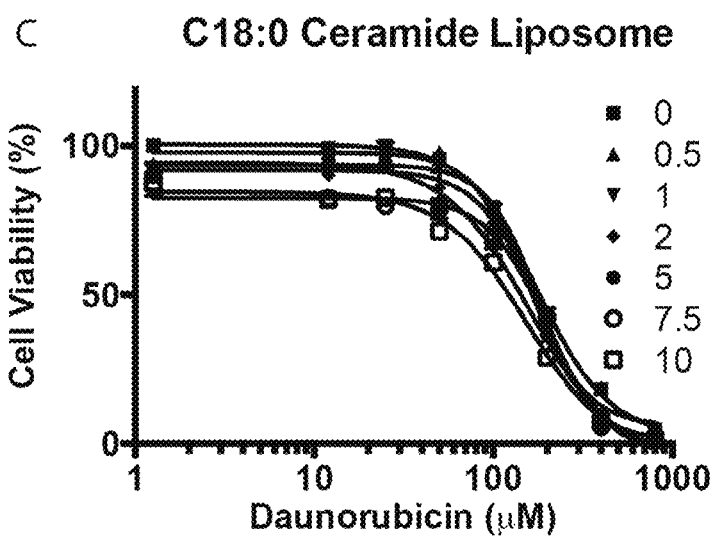
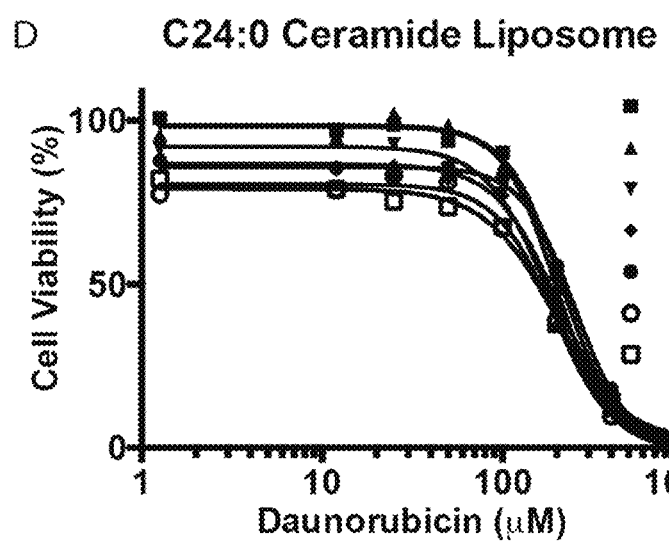
FIGURE16C-D

CERAMIDE REVERSAL OF MULTI-DRUG RESISTANCE

This application is a continuation-in-part of PCT/US2014/028828 filed Mar. 14, 2014 and published on Sep. 18, 2014 as WO 2014/144421 and claims the priority of U.S. provisional application No. 61/794,584 filed Mar. 15, 2013. The contents of each application are hereby incorporated by reference in their entirety into the instant application.

FIELD OF THE INVENTION

The invention relates to compositions and methods for the reversal of multi-drug resistance in cells that overexpress the lipid transporter, P-glycoprotein (P-gp). More particularly, the invention relates to C16:0 ceramide-based nano-liposomes which restore vesicular trafficking in these cells.

BACKGROUND OF THE INVENTION

Cells with multidrug resistance (MDR) due to aberrant expression of the lipid transporter P-glycoprotein (P-gp) display a wide range of biochemical changes that affect membrane lipid composition. Despite an established role for sphingomyelin (SM) as precursor to the pro-apoptotic second messenger ceramide in the action of numerous chemotherapeutic drugs, there has not been a major focus on the potential role of altered SM metabolism in P-gp action.

P-gp (ABCB1) is a member of the ATP-binding cassette (ABC) superfamily, which exports structurally diverse hydrophobic compounds from cells, driven by ATP hydrolysis (4). P-gp overexpression is considered to drive efflux of chemotherapeutic drugs in human cancers, leading to MDR. P-gp substrates partition into the lipid bilayer before interacting with P-gp, which has been proposed to act like a hydrophobic vacuum cleaner. Functionally, P-gp acts as an outwardly-directed phospholipid and sphingolipid flippase, suggesting it translocates drugs from the inner to the outer leaflet of the plasma membrane. Cancers considered chemoresistant such as renal cell, adrenocortical and colon cancer often display spontaneously high levels of P-gp, while other cancers such as leukemias develop high P-gp expression during therapy.

While P-gp MDR has often been associated with increased glucosylceramide synthase activity and increased glucosyl-ceramide, which mislocalizes to plasma membrane, a detailed analysis of the sphingomyelin/ceramide axis in cells displaying P-gp-mediated MDR has not been published. Furthermore, despite significant clinical effort, no effective therapy currently exists to reverse P-gp-mediated MDR in human cancers. Thus, the need exists for methods and compositions to overcome chemoresistance.

SUMMARY OF THE INVENTION

The present invention is based on the observation that chemoresistance, as the result of mislocalization of drugs that ordinarily traffic to the nucleus, can be reversed by the provision of exogenous sphingomyelinase or ceramide C16:0 to the cell.

In one aspect, therefore, the present invention relates to methods and compositions for reversing multidrug resistance (MDR) in P-gp-overexpressing cancer/tumor cells by restoring vesicular trafficking in the cell. The method comprises the administration of a fusogenic ceramide that self-aggregates, such as C16:0.

In a related aspect, the invention relates to a method for inducing in cancer cells that overexpress P-glycoprotein (P-gp) nuclear trafficking of a therapeutic agent from the cytoplasm of the cell where it is "hung up" in acidic vesicles to the nucleus thereby reversing multi-drug resistance (MDR), the method comprising contacting said cancer cells with a fusogenic ceramide, such as C16:0-ceramide.

In a further related aspect, the invention relates to nano-liposomes comprising C16:0 ceramide capable of restoring trafficking in the resistant cell. In one embodiment, the nano-liposome is stably associated with at least one therapeutic agent, for example, an anthracycline antibiotic (daunorubicin or doxorubicin), vinca alkaloid or other chemotherapeutic agent. The C16:0 ceramide is present in the nano-liposome in an amount between 1% and 25% of said total lipid composition of said liposome in order to facilitate fusion of cytoplasmic vesicles containing the chemotherapeutic agent to the nuclear membrane followed by diffusion of the chemotherapeutic agent into the nuclear core.

In yet another aspect, the invention relates to a method for predicting whether a cell or tumor is MDR, the method comprising determining the level of at least one of sphingomyelin, P-gp and ceramide of the cell or tumor, wherein an increased level of any of sphingomyelin, P-gp and ceramide indicates MDR.

In a related aspect, therefore, the invention relates to a method for selecting a treatment option for a subject, wherein the method comprises determining the expression levels of sphingomyelin, or P-gp in a tumor cell from the subject and selecting a treatment option that includes administration of N-palmitoyl (C16:0) ceramide when levels of any of sphingomyelin, or P-gp are elevated when compared to levels in non-resistant cells.

In another aspect, therefore, the invention relates to a composition or nano-liposome comprising a long N-acyl chain ceramide. Exposure to exogenous ceramide or a nano-liposome comprising long N-acyl chain ceramide, for example, long chain N-palmitoyl (C16:0) ceramide, can be used to reverse MDR chemoresistance. The composition or nano-liposome comprising ceramide may further comprise a therapeutic agent such as doxorubicin, daunorubicin, vincristine, cisplatin etc.

In yet another aspect, the invention relates to a method for selective treatment of cancers that express high lipid transporter P-glycoprotein (P-gp) levels, the method comprising: administering to a subject in need thereof a composition comprising a ceramide-based nano-liposome and a therapeutic agent.

A method for the selection of appropriate treatment for a subject, the method comprising determining the levels of lipid transporter P-glycoprotein (P-gp) in a tumor or tumor cell from the subject; Identifying the tumor or tumor cell as MDR if levels of P-gp are elevated in comparison to levels in cells that are not MDR; and administering exogenous ceramide to a subject identified as MDR.

BRIEF DESCRIPTION OF THE DRAWINGS

FIG. 2 shows that sphingomyelin and ceramide levels are increased in MDR cells. Sphingomyelin content in parental (DC-3F and P388/O) and MDR (ADX and P388/DX) cell lines was measured using the phospholipid phosphorus assay. Ceramide levels in each cell line were determined by DAG kinase assay. Data (mean±S.E.) are compiled from three experiments performed in duplicate. *p<0.01 versus parental cell line (DC-3F and P388/O, respectively).

FIG. 3 shows increased sphingomyelin content in ADX cells is located in plasma membranes. Time course of [$^3$H]sphingomyelin degradation (top) and [$^3$H]ceramide generation (bottom) in ADX cells radiolabeled with [$^3$H] choline chloride to isotopic equilibrium and treated with *B. cereus* SMase (0.50 U/ml). Data (mean±S.E.) are compiled from three studies performed in duplicate.

FIG. 4A-D show that SMase treatment induces ceramide generation and cell death in ADX cells. A, time course of sphingomyelin changes in DC-3F and ADX cells after *B. cereus* SMase (0.05 U/mL) treatment. B, time course of ceramide generation. C, DC-3F and ADX cells were treated with increasing doses of *B. cereus* SMase (0-2 U/mL) and cell survival was measured by MTT (3-(4,5-dimethylthiazol-2-yl)-2,5-diphenyltetrazolium bromide) tetrazolium reduction (MTT) assay. D, Cells were seeded in 96-well plates (2×10$^3$ cells/well) in a 0.1 ml DME:F12 medium containing 5% FBS and cultured at 37° C. for 24 hours before addition of daunorubicin. After 2 h, *B. cereus* SMase (0.0-0.5 U/ml was added. After 1 day, DC-3F (upper panel) and ADX (lower panel) cell survival was measured by MTT assay. SMase alone had minimal impact on cell survival. Data are from one representative of three independent studies.

FIG. 5 shows that daunorubicin localizes differently in drug sensitive and drug resistant cells. Drug sensitive cells, P388/O and DC-3F, and drug resistant cells, P388/Dox and ADX, were grown on a 4-well slide and treated with daunorubicin (20 μM) for 2 h. Cells were examined using an Axio Zeiss fluorescence microscope.

FIGS. 16A-D show the impact of ceramide-containing liposomes on viability of daunorubicin-loaded ADX cells. A-D: ADX cells were pre-loaded for 2 hours with daunorubicin (20 µM) and then incubated with plain (A) or ceramide-based liposomes (µM), C16:0-(B), C18:0-(C), 024:0 (D) at escalating concentrations as indicated by symbols in the right column of panel B-D. Impact on cell viability by MTT assay was assessed after 8 hours. Control incubations received equivalent amounts of liposomes lacking ceramides.

DETAILED DESCRIPTION OF THE INVENTION

All patents, applications, publications and other references cited herein are hereby incorporated by reference in their entirety into the present application.

Presuming that competitive inhibition of drug efflux would chemosensitize, cinical trials to reverse the P-glycoprotein (Pgp)-mediated multi-drug (MDR) phenotype have almost always utilized competitive inhibitors of P-gp transporter function, and have largely failed. It is now known that even if drug efflux were prevented, unless strategies were adopted to reverse the trafficking defect, drug would still not reach intended nuclear targets.

The present disclosure identifies a previously unrecognized multi-step sphingolipid-regulated vesicular transport system that when dysregulated plays a fundamental role in chemoresistance.

The present invention is based on the observation that a specific ceramide species, C16:0 ceramide, delivered by nano-liposome, reverses this defect, permitting rapid translocation of an anti-cancer therapeutic from cytoplasmic vesicles to the nucleus in MDR cells. Thus, it provides a therapy that specifically targets tumors associated with overexpression of the lipid transporter, P-glycoprotein.

The present disclosure describes studies that define the vesicular phenotype for the first time and its ceramide-mediated trafficking to the nucleus. The daunorubicin (DNR)/doxorubicin (Dox)-containing vesicle in MDR cells is acidic, dispersed throughout the cytoplasm, and contains the MDR mediator ABCB1 (P-gp) in its membrane. Upon provision of C16:0 ceramide, time lapse photography defined a multi-step process in which Dox- and ABCB1-containing vesicles traffic to a peri-nuclear location, fuse with nuclear membranes, and thereafter Dox diffuses into the nuclear core while ABCB1 remains in the nuclear membrane. Other long chain and very long chain ceramides fail to confer chemosensitivity.

ADX MDR tumor cells, like ADX cells in culture, fail to traffic Dox to the nucleus in vivo, as Dox gets "hung up" in an acidic vesicle in the cytoplasm. In one embodiment, C16:0 ceramide-containing nano-liposomes restore multi-step drug trafficking into the nucleus and restore chemosensitivity.

MDR cells (for example, ADX, actinomycin-selected Chinese hamster lung fibroblast and P388/Dx, doxorubicin-selected murine P388 leukemia cells) exhibit constitutive activation of the de novo pathway of ceramide synthesis as a result of enhanced serine palmitoyltransferase (SPT) activity, resulting in increased ceramide content.

P-gp and Sphingomyelin/Ceramide Abnormalities

Figure 1:
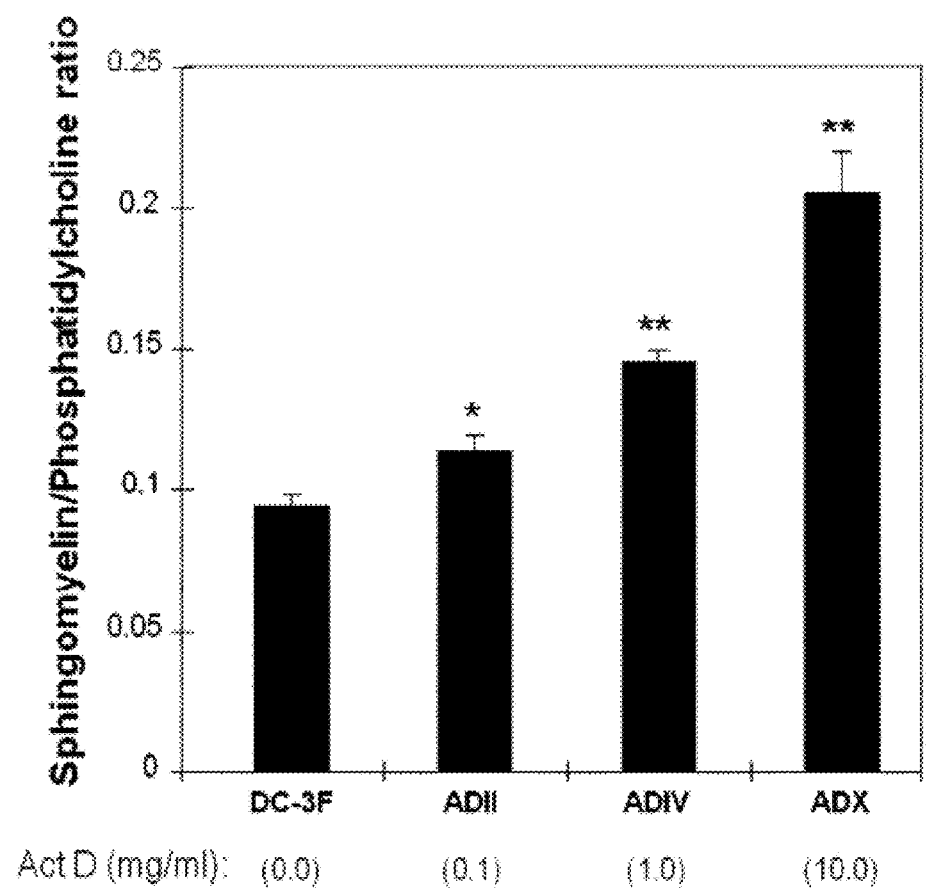
FIG. 1 shows that sphingomyelin levels are increased in MDR cells. Cells (DC-3F and MDR derivatives ADII, ADIV, ADX) were labeled to isotopic equilibrium with [$^3$H]choline chloride (1 mCi/ml) and levels of radiolabled sphingomyelin and phosphatidylcholine were measured. Concentrations of actinomycin D used for selection are indicated in brackets. Data (mean±S.E.) are compiled from three experiments performed in duplicate.

As sphingomyelin/ceramide signaling of apoptosis is often associated with cancer therapies, and as P-gp is a sphingolipid transporter, we profiled the sphingolipid/ceramide composition of two isogenic sets of MDR cell lines: the hamster lung fibroblast DC-3F actinomycin-selected lines, and the P388 doxorubicin-selected leukemia lines. FIG. 1 shows, using a matched set of DC-3F and actinomycin D resistant lines (ADII-ADX) in which P-gp levels have been shown to linearly relate to levels of actinomycin D resistance (not shown), that sphingomyelin levels correlate directly with extent of resistance. Furthermore, a second P-gp MDR line the P388/Dx line also shows sphingomyelin accumulation, and both ADX and P-gp display increased total ceramide (FIG. 2). A detailed analysis of all of the major enzyme activities of the de novo sphingomyelin synthetic pathway revealed selective upregulation of serine palmitoyltransferase activity, the regulatory enzyme for the synthesis of sphingoid base, the first step in sphingolipid synthesis, in addition to the anticipated increase in glucosylceramide synthase activity, a hallmark of the P-gp MDR phenotype (Table 1).

TABLE 1

|  | DC-3F | ADX |
| --- | --- | --- |
| SPT (pmol/mg · min) | 8.32 ± 0.44 | 13.58 ± 0.68* |
| CS (pmol/µg · h) | 12.30 ± 0.28 | 10.88 ± 0.44 |
| ASMase (pmol/µg · h) | 7.61 ± 0.17 | 7.81 ± 0.14 |
| NSMase (pmol/µg · h) | 0.431 ± 0.031 | 0.428 ± 0.023 |

TABLE 1-continued

|  | DC-3F | ADX |
|---|---|---|
| SMS (pmol/μg · h) | 1.81 ± 0.12 | 1.95 ± 0.15 |
| GCS (pmol/μg · h) | 4.03 ± 0.40 | 13.21 ± 0.17* |
| nCDase (pmol/μg · h) | 2.01 ± 0.28 | 1.77 ± 0.16 |
| aCDase (pmol/μg · h) | n.d. | n.d. |

Table 1 shows that the ceramide de novo synthesis pathway is activated in ADX MDR cells. Sphingomyelin mass was measured by phospholipid phosphorus assay and ceramide by the diacylglycerol kinase (DAG) assay. Enzymatic activities were performed as standardized. Data (mean±S.E.) are compiled from at least three experiments performed in duplicate. n.d. activity not detected. *p<0.01 versus DC-3F cells. SPT: Serine palmitoyltransferase, CS: ceramide synthase, ASMase: acid sphingomyelinase, NSMase: neutral sphingomyelinase, GCS: glucocylceramide synthase, nCDase: neutral ceramidase, aCDase; alkaline ceramidase.

Sphingomyelin and MDR

FIG. 3 shows that there is a direct relationship between sphingomyelin abnormalities and MDR. Whereas parental DC-3F cells are highly sensitive to daunorubicin (EC50=0.8 μM), ADX cells are chemoresistant (EC50=92 μM). Treatment of ADX cells with increasing doses of exogenous sphingomyelinase, to generate an endogenous ceramide load (data not shown), a standard technique in the field, resulted in dose-dependent reduction in the EC50 to 4 μM. In contrast, DC-3F cells were unaffected by sphingomyelinase treatment. Furthermore, chemosensitization of ADX cells was also achieved for vincristine and cis-platinum, while no sensitization was achieved for staurosporine, a P-gp-independent apoptosis-inducer (not shown). These studies indicate that sphingomyelin hydrolysis and/or ceramide generation reverses the MDR phenotype.

Figure 4C:
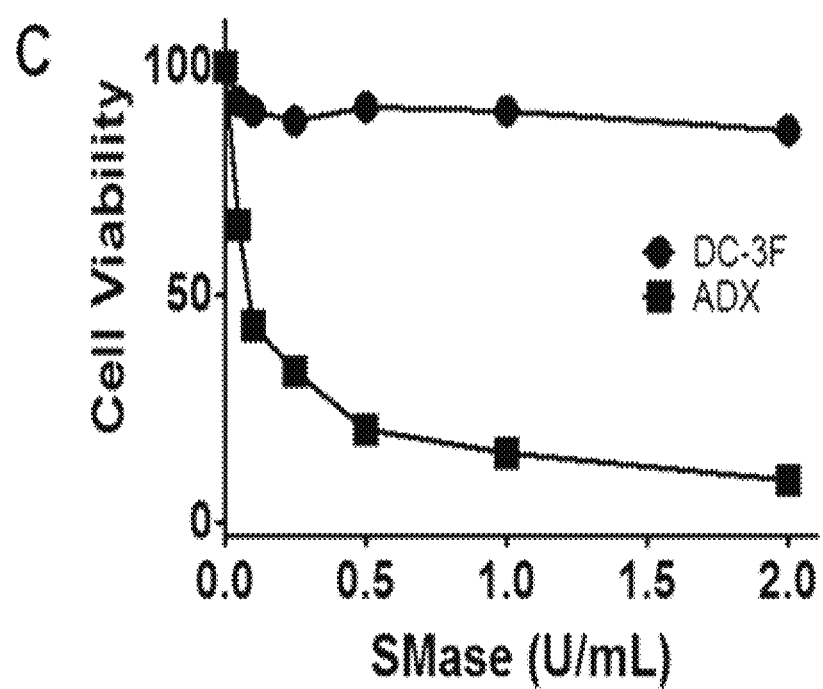
Figure 4D:
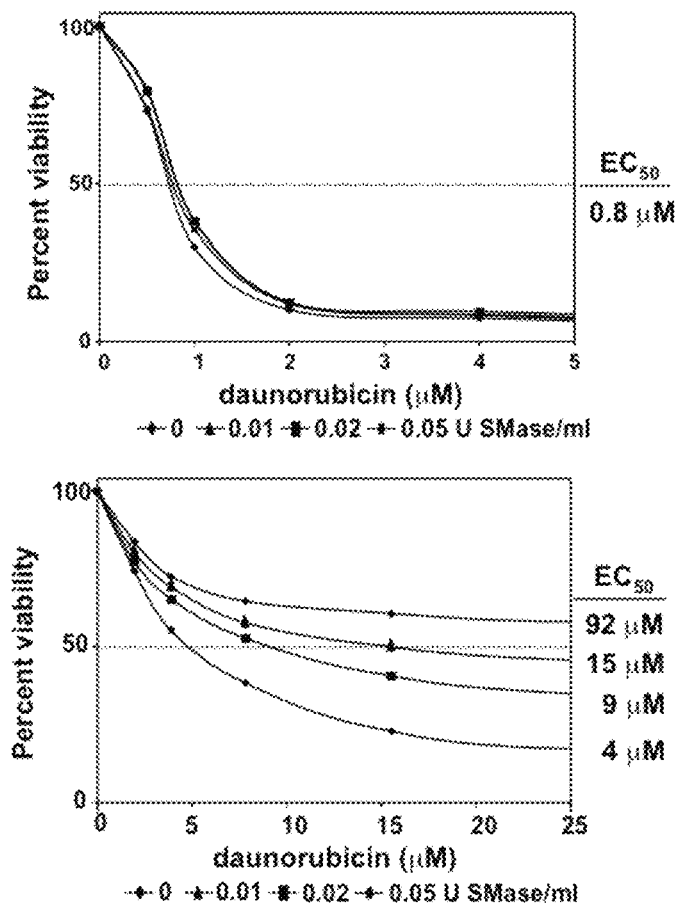

FIG. 3 shows increased sphingomyelin content in ADX cells is located in plasma membranes. FIG. 4 show that the sphingomyelin accumulation in MDR cells is on the cell surface as it is amenable to exogenous bacterial ASMase degradation into ceramide In contrast, DC-3F cells were unaffected by sphingomyelinase treatment. Further, as the amount of ceramide generated is large the MDR but not the parental cells undergo ASMase-induced apoptotic death (FIG. 4C).

Anti-cancer Therapeutics Including Anthracycline Antibiotics

Anthracycline antibiotics such as daunorubicin and doxorubicin and their derivatives are known antineoplastic agents produced by the fungus *Streptomyces peucetius*. Evaluation of the mechanism of daunorubicin resistance in sphingolipid-disordered ADX cells revealed that drug traffics to the nucleus of daunorubicin-sensitive parental DC-3F cells, whereas it mislocalizes into large cytoplasmic vacuoles in ADX MDR cells. Furthermore, application of small amounts of exogenous acid sphingomyelinase to generate endogenous ceramide, or provision of exogenous long-chain natural C16-ceramide, result in rapid translocation of vacuolar daunorubicin into the nucleus and 25-fold enhance cell kill. It would appear therefore that MDR chemoresistance results in part from failure to generate the fusogenic lipid ceramide in a vesicular trafficking system that normally transports daunorubicin into the nucleus.

Daunorubicin is Retained in Cytoplasmic Vesicles in ADX MDR Cells

Figure 6A:
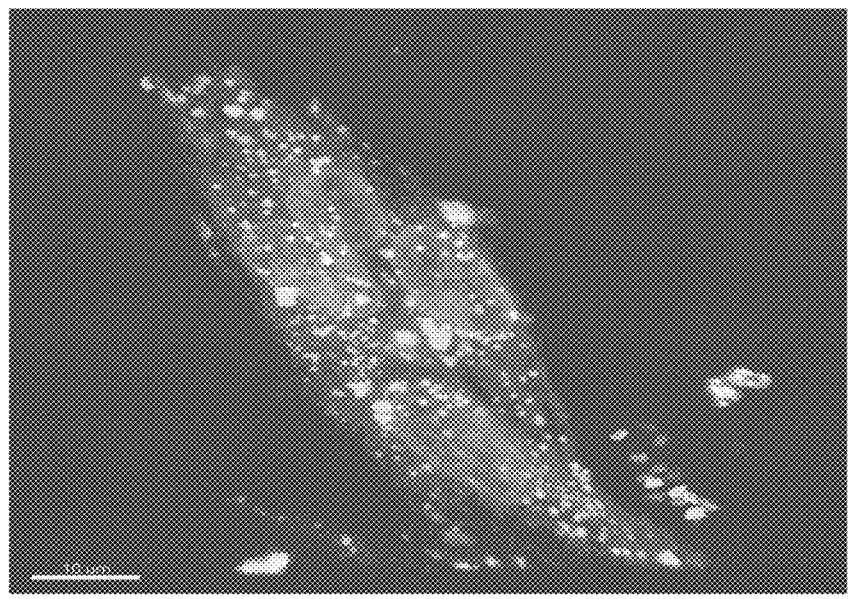
FIGS. 6A and 6B show that daunorubicin localizes to vesicles in multidrug resistant cells. ADX cells were grown on a 4-well slide, 20 μM daunorubicin was added for 90 min, followed by 1 μg/mL Hoechst for 30 min. Confocal images were taken with a Leica SP5-Inv instrument. Daunorubicin was excited at 515 nm and emission fluorescence was collected from 640-740 nm, while Hoechst was excited at 405 nm and emission collected from 440-500 nm.
Figure 6B:
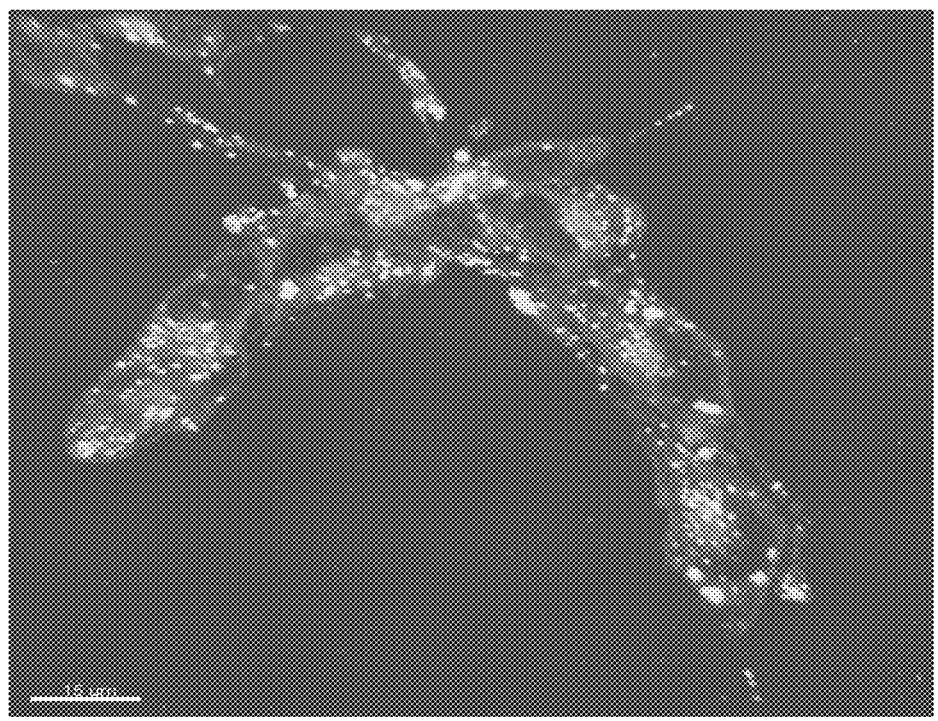

To confirm that daunorubicin traffics incorrectly in MDR cells we took advantage of the spontaneous fluorescence of anthracyclines. Whereas daunorubicin traffics to the nucleus where it finds its DNA/RNA substrates in parental chemosensitive DC-3F and P388/O cells, daunorubicin is "hung up" in cytoplasmic vesicles in ADX and P388/Dox MDR cells (FIG. 5, higher magnification see FIG. 6).

Figure 7A:
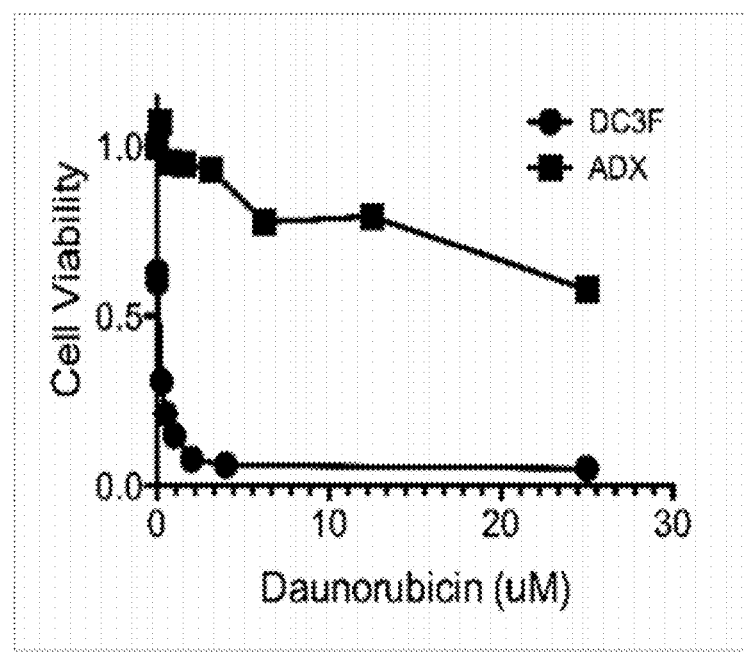
FIGS. 7A and 7B show that sub-lethal SMase sensitizes MDR cells to daunorubicin treatment. A, DC-3F and ADX cells were treated with increasing doses of daunorubicin. B, DC-3F and ADX cells were incubated with *B. cereus* SMase (0.0-0.05 U/ml) and treated with daunorubicin for 1 day. Cell survival was measured by MTT assay. Data are from one representative of three independent studies.
Figure 7B:
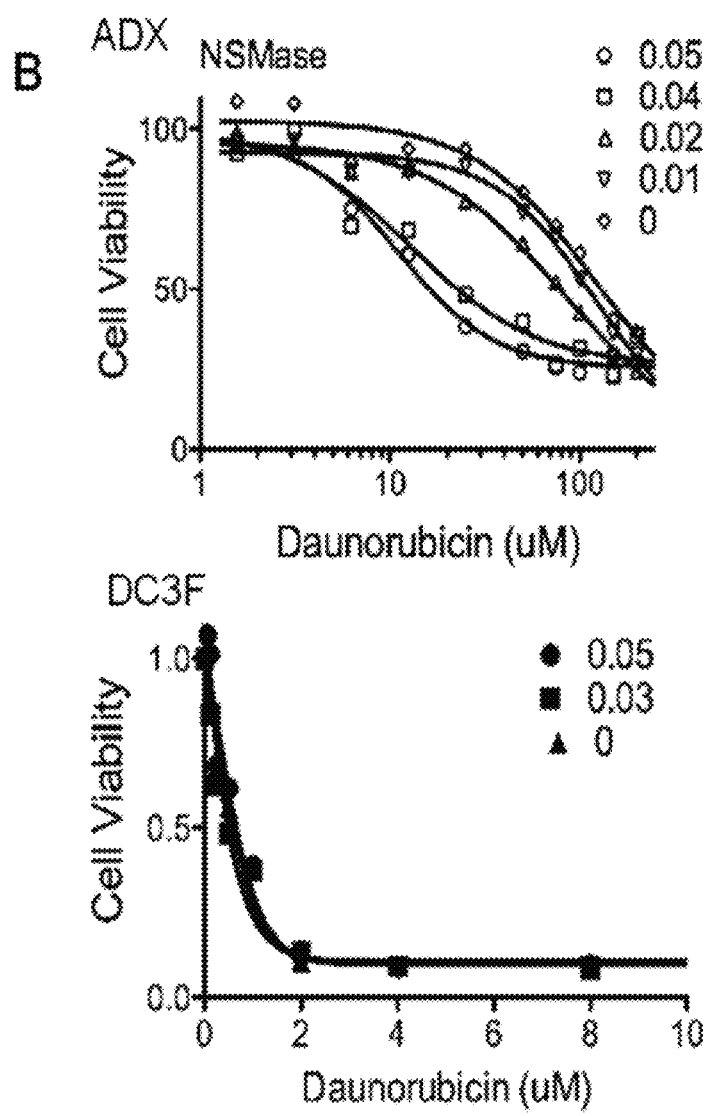
Figure 8A:
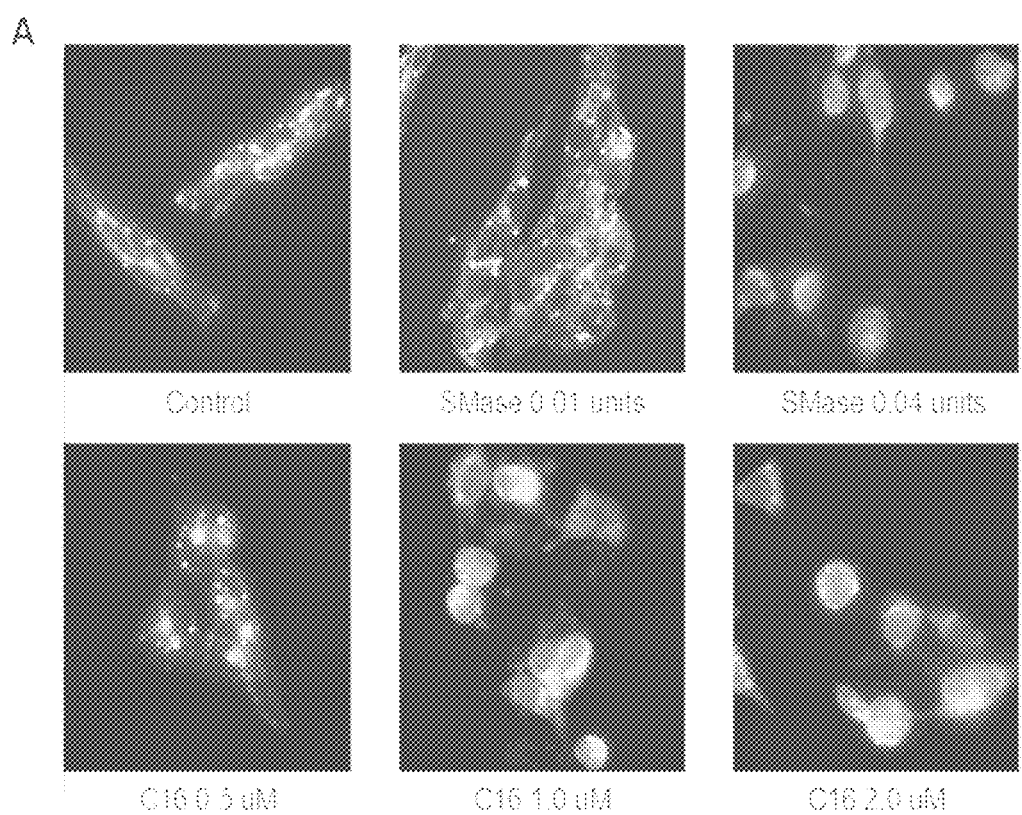
FIGS. 8A and 8B show sub-lethal SMase or ceramide induce daunorubicin trafficking into the nucleus of ADX MDR cells. ADX cells were grown on 4-well slides. Panel A, After 20 uM daunorubicin was added for 90 min, SMase (0.01 or 0.04 U/ml) or C16 ceramide (0.5, 1, or 2 uM) were added. Cells were examined under Axio Zeiss fluorescence. Panel B, Cell were treated as in A and examined using a Leica SP-5 inverted confocal microscope. Imaris software from BitPlane was used to construct 3D images.
Figure 8B:
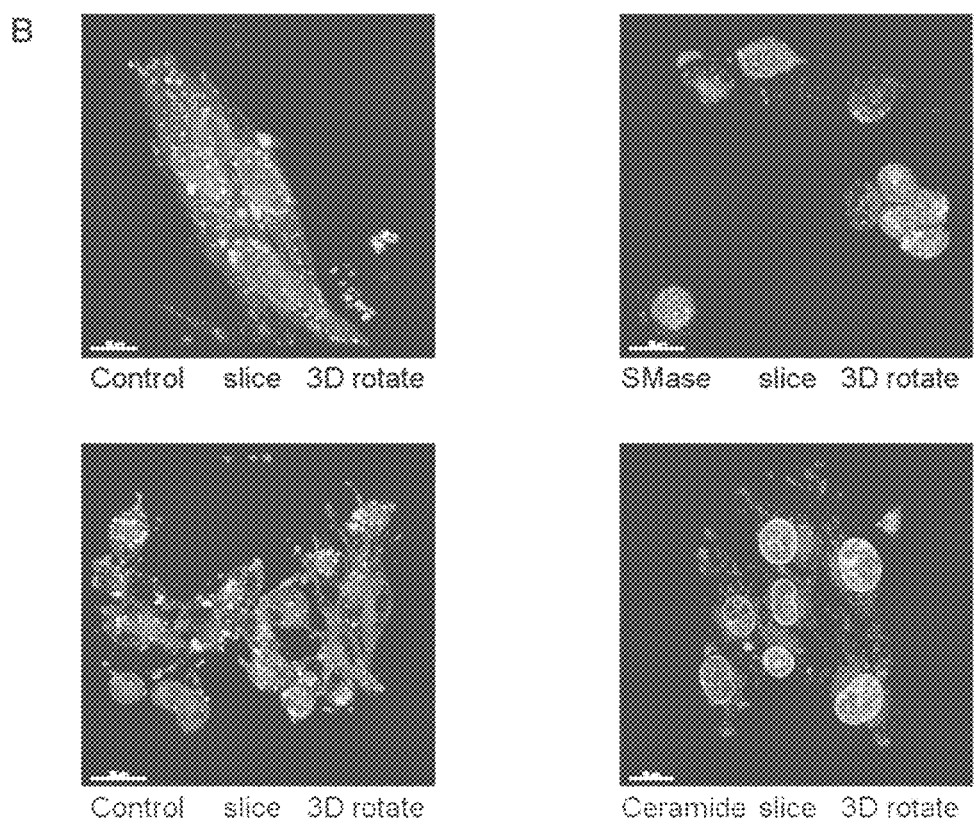
Figure 9A:
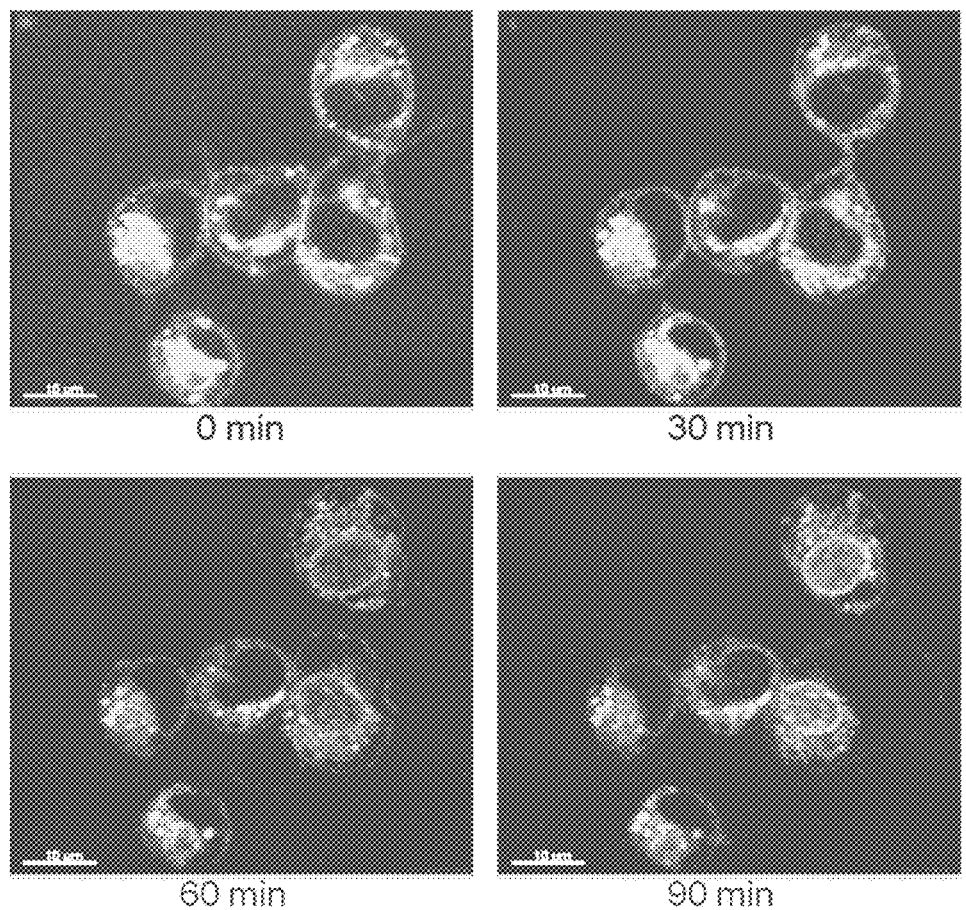
FIGS. 9A-C show the time course of SMase-induced daunorubicin trafficking into the nucleus of MDR cells. ADX cells were grown on 4-well slides, 50 μM daunorubicin was added for 90 min, followed by 0.05 U/mL of SMase. Cells were examined under Leica SP-5 inverted confocal microscope and images acquired every min for 90 min. Imaris software from BitPlane was used to generate the movie. A, representative images of ADX cells after daunorubicin and SMase treatment. B, a movie that shows drug trafficking from cytosol into the nucleus. C, DC-F3 parental cells accumulate daunorubicin (50 μM) after 2 h in the nucleus, whereas ADX MDR cells display a drug accumulation in cytoplasmic vesicles detected by standard fluorescence microscopy. Upon treatment with SMase for 30-9-min. or C16:0 ceramide for 60 min., daunorubicin trafficked to the nucleus.
Figure 9B:
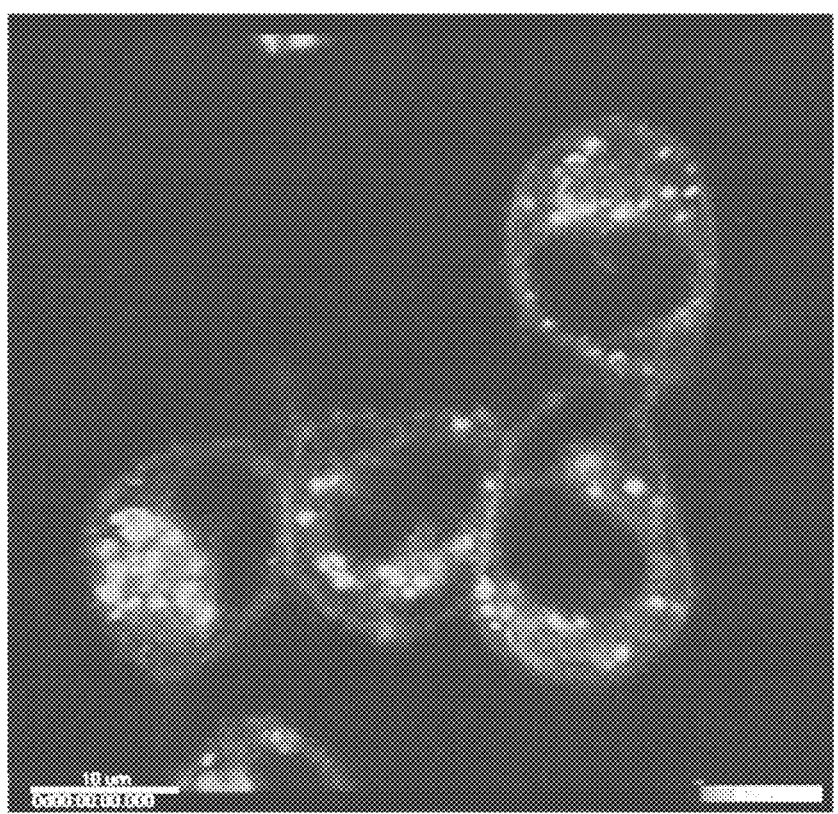
Figure 9C:
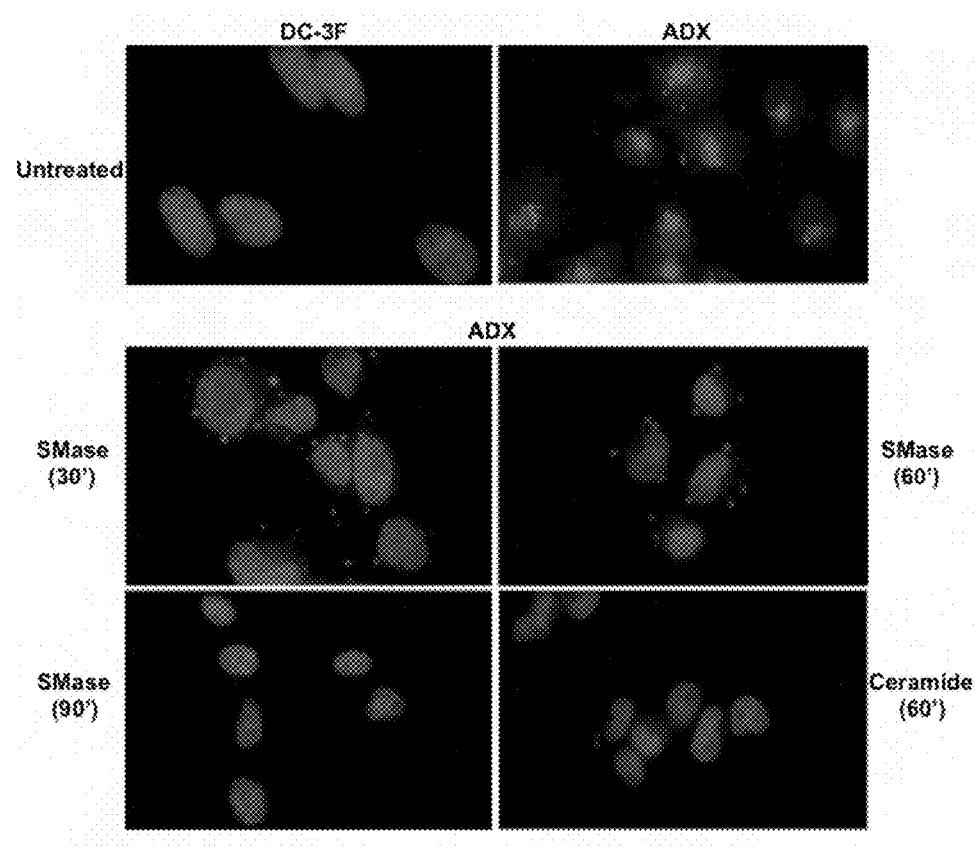
Figure 10:
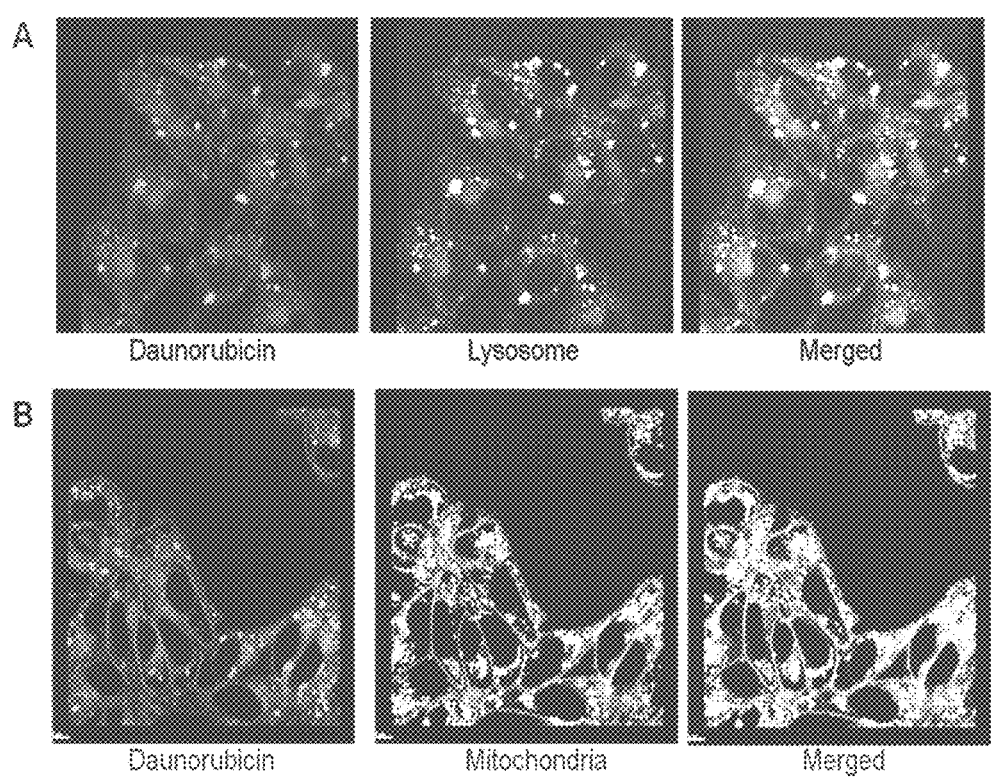
FIG. 10 show that daunorubicin accumulates in an acidic compartment. ADX cells were grown on 4 well slides, 20 μM daunorubicin was added for 90 min, 50 nM lysotracker (Panel A) or 100 nM mitotracker (Panel B) were added and images were taken with Leica-5 inverted confocal microscope.

Upon incubation of ADX MDR cells with 20 μm daunorubicin, we found 38±6 vesicles per cell with a mean diameter of 0.67±0.01 μM at steady-state at 2 hours. Provision of small non-apoptotic quantities of exogenous sphingomyelinase reverses chemoresistance (FIG. 7B, Table 3), as does long chain pro-apoptotic C16:0 natural ceramide (FIG. 14), and both cause rapid trafficking of daunorubicin-containing vesicles to the nucleus, fusion with the nuclear membrane and dumping of their chemotherapeutic cargo into the nucleus (FIGS. 8A, B). Videography reveals this event occurs over 30-60 min.

Ceramide-based Liposomes for Reversal of MDR

Natural ceramides are categorized into long N-acyl chain (C16:0-C20:0) and very long N-acyl chain (C22:0-C24:1) species dependent on the fatty acid covalently attached by amide linkage to the primary amine at C-2 of the sphingosine backbone. We recently showed that different N-acyl chain ceramide species possess distinct biologic attributes with long chain N-palmitoyl (C16:0) ceramide being pro-apoptotic, while very long chain C24:0, C24:1 ceramides are anti-apoptotic (1).

Ceramide is one of the most hydrophobic molecules in mammalian cells, hence it cannot be delivered "naked" as it phase separates in aqueous suspension such as in blood (note that in cell culture an organic solvent, dodecane, can be used to suspend natural ceramides for cellular uptake). In one embodiment, a set of ceramide-based nano-liposomes were constructed by extrusion technology. These nano-liposomes contain 2 μM (10 mol %) ceramide in the bilayer and are, on average, in the range of about 50-200 nM; in one embodiment the nano-liposomes are 93±28 nM (mean±SD) as determined by dynamic light scattering (DLS) analysis.

C16-ceramide was chosen as the starting point since there is a body of work indicating this ceramide is the most-often generated ceramide by anti-cancer agents (1, 5). Further, it was shown that this ceramide species has self-associating fusogenic properties, generating large non-bilayer macrodomains in mammalian bilayers, sites of protein oligomerization for apoptosis induction (6). No other ceramide appears to possess this attribute.

Figure 11:
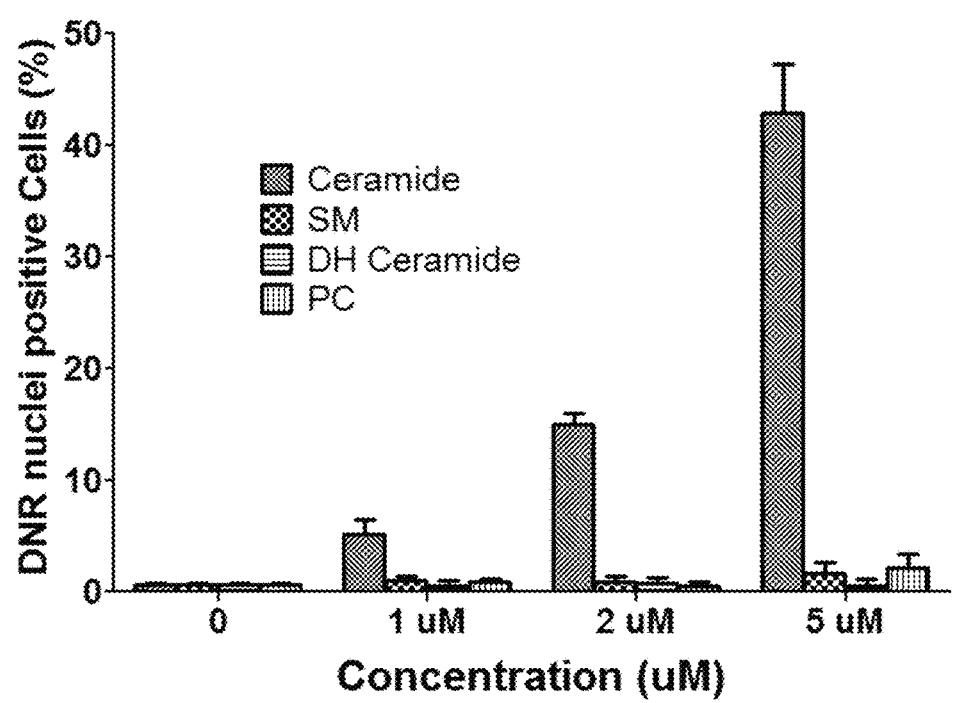
FIG. 11 shows that daunorubicin nuclear accumulation is ceramide specific. ADX cells were grown on 4-well slides, 20 uM daunorubicin was added for 90 min, followed by various dose of liposomes containing C16:0 ceramide, sphingomyelin, C16:0 dihydroceramide or phosphatidylcholine for 1 h. Cells were examined under Leica SP-5 inverted confocal microscope. Y axis represents percent of cells with nuclear drug.
Figure 12:
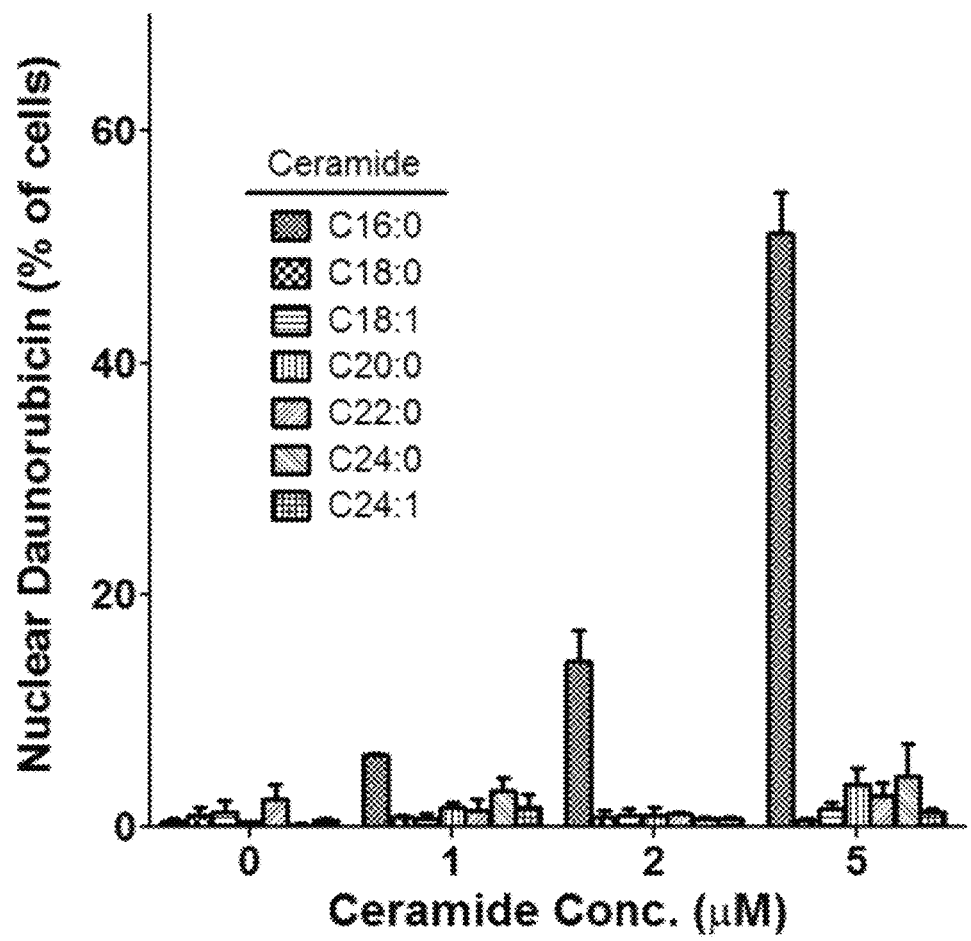
FIG. 12 shows that induction of daunorubicin trafficking into the nucleus of MDR cells is C16:0 ceramide specific. ADX cells were grown on 4-well slides. 3.5×104 ADX cells were incubated with 20 μM daunorubicin in DMEM HG:F-12 medium without serum. After 2 hours, at which time daunorubicin had reached steady state accumulation in cytoplasmic vesicles, liposomes containing long and very long chain ceramides were added to cells at 0, 1, 2, and 5 μM. After a 1 hour-incubation at 37° C., nuclear localization of daunorubicin was determined by confocal microscopy. Cells were examined under Leica SP-5 inverted confocal microscope. Y axis represents percent of cells with nuclear drug.

FIG. 11 shows that incubation of ADX cells pre-loaded with daunorubicin with C16-ceramide-containing nano-liposomes, but not other closely related lipid containing liposomes, results in rapid trafficking of daunorubicin into the nucleus, a pre-requisite for cell death induction. In more recent preliminary studies, a direct comparison of the different long chain (C16:0-C20:0) and very long chain (C22:0-C24:1) ceramides revealed that only C16:0 ceramide-containing liposomes appeared to possess this vesicular trafficking property (FIG. 12).

Nano-liposomes

In another aspect of this invention, there is provided a nanoliposome comprising C16:0 ceramide, and in some embodiments also encapsulating a chemotherapeutic agent, characterized in that the nanoliposome has a diameter in the range of 50-200 nm, in one embodiment, 75-175 nm, in another embodiment, 100-150 nm, and has the structure of a small unilamellar vesicle; the chemotherapeutic agent encapsulated in the nanoliposome has an activity corresponding to 90-100% of that of the agent prior to encapsulation.

Nanoliposomes can be prepared in accordance with methods known to those of skill in the art, for example, as described in Liposomes: Rational Design (A. S. Janoff, ed., Marcel Dekker, Inc., New York, N.Y.) Additionally, a liposome preparation comprising doxorubicin is described in WO2006/051549 (for purposes of preparing liposomes for use in the methods disclosed herein, the contents of each of these references is incorporated by reference into the present application.) Suitable nanoliposome preparation methods include ether injection method, the surfactant method, the freeze-thaw method, the reverse-phase evaporation method, the ultrasonic treatment method, the ethanol injection method, the extrusion method and the French press method.

In one embodiment, the nanoliposome of the invention is prepared by the extrusion method. The extrusion method involves first combining lipids in chloroform to give a desired molar ratio. The resulting mixture is dried under a stream of nitrogen gas and placed in a vacuum pump until the solvent is substantially removed. The samples are then hydrated in an appropriate buffer or mixture of therapeutic agent or agents. The mixture is then passed through an extrusion apparatus to obtain liposomes of a defined average size. Average liposome size can be determined by dynamic light scattering using, for example, a ZetaSizer (Malvern, Westborough, Mass.).

Liposomes for use in the present invention may be prepared with surface stabilizing hydrophilic polymer-lipid conjugates such as polyethylene glycol-lipid, to enhance circulation longevity.

In one embodiment, liposomes comprised of approximately 20 μmol total lipid, containing 82.5/7.5/10 mol/mol of fully hydrogenated soybean phosphatidylcholine (HSPC)/ N-carbamyl-poly-(ethylene glycol methyl ether)-1,2-distearoyl-sn-glyco-3-phosphoethanolamine (2kPEG-DSPE)/ ceramide, are generated as follows.

Each lipid is solubilized at 10 mg/ml in chloroform and transferred into a round bottomed flask, dried under nitrogen while rotating, and lyophilized at least 2 h to remove trace chloroform. Lipid films are hydrated for 1 h at 65° C. in 1 ml PBS. During hydration, three cycles of 15-second sonication are performed every 20 min. The hydrated lipid film thereafter undergoes three cycles of freezing (at −78° C. using dry ice in isopropanol×5 min) and thawing (at 65° C.×10 min) to obtain multilamellar liposomes. Large unilamellar nano-liposomes are obtained by extrusion of multilamellar liposomes 11 times through a 0.1 μm pore size polycarbonate membrane filter using the extrusion syringe system from Avanti Polar Lipids. A 20-fold diluted liposome (50 μl liposome in 950 μl PBS) is used to confirm size distribution by dynamic light scattering (ZetaSizer, Malvern).

Restoration of Daunorubicin Vesicular Trafficking Via Ceramide-based Liposomes

C16:0-ceramide was identified as a pro-apoptotic ceramide species generated post-irradiation in HeLa cells (and now in numerous other cells and tissues), whereas the other two ceramides generated, C24:0 and C24:1 ceramide, were found to be anti-apoptotic (1). Currently, C16:0 ceramide appears to be the only natural ceramide capable of inducing fusion of drug-containing MDR vesicles with nuclear membranes; some non-natural hydrophilic ceramides have been shown to induce nuclear daunorubicin transfer, albeit less effectively than C16:0 (Table 2).

TABLE 2

| Ceramide Species | Concentration | | |
|---|---|---|---|
| | 1 μM | 2 μM | 5 μM |
| C2:0 | 7.5 ± 2.5 | 12.5 ± 3.3 | 7.0 ± 1.6 |
| C4:0 | 8.0 ± 2.4 | 11.9 ± 2.7 | 13.0 ± 2.1 |
| C6:0 | 8.8 ± 2.4 | 12.2 ± 2.0 | 16.2 ± 2.3 |
| C8:0 | 11.4 ± 1.9 | 19.8 ± 2.1 | 35.5 ± 2.4 |
| C10:0 | 6.8 ± 2.2 | 13.1 ± 2.8 | 20.0 ± 2.4 |
| C12:0 | 8.9 ± 3.0 | 18.8 ± 3.2 | 22.3 ± 3.1 |
| C14:0 | 7.4 ± 2.4 | 17.6 ± 3.4 | 23.4 ± 3.2 |
| C16:0 | 13.9 ± 1.7* | 24.3 ± 2.0* | 48.3 ± 2.7* |

Data (Mean ± 95% CI) represents percent of ADX cells displaying nuclear daunorubicin.
*p < 0.001 C16:0 vs. other ceramide species each Fusion of MDR-containing drug vesicles with the nuclear membrane and deposition of cargo can be detected by conventional confocal microscopy or in real-time by confocal videography tracking daunorubicin fluorescence. In ADX cells, the timing and dose-response capabilities of natural ceramide-containing nano-liposomes to induce fusion and enhance cell death is investigated using techniques established in our lab.

Figure 13:
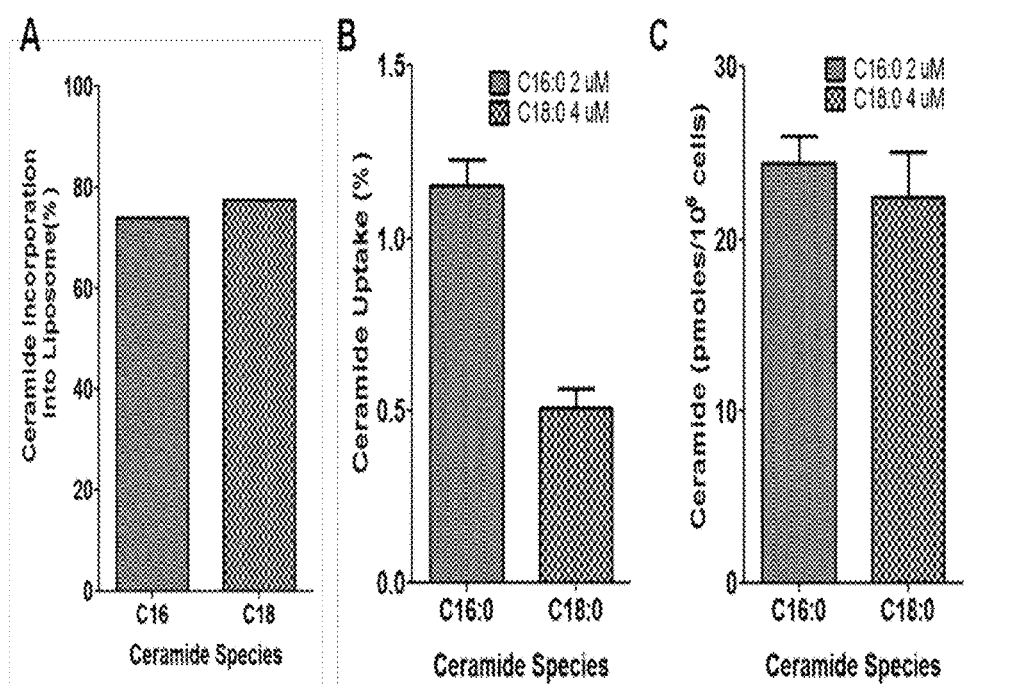
FIG. 13 shows that C18:0 ceramide is taken up by ADX cells. Panel A, $^3$H-labeled C16:0 and C18:0 ceramides incorporate into liposomes to the same extent. Panel B and Panel C, ADX cells grown on 4-well slides were treated for 2 h with $^3$H-labeled ceramide-containing liposomes. After media was washed out, $^3$H was counted using scintillation counter. Panels B and C show that C18:0 ceramide is taken up by cells about 50% as efficiently as C16:0 ceramide indicating failure of 018:0 ceramide to reverse MDR is not due to failure to transfer from liposomes into drug-resistant cells.

We have generated ceramide-containing liposomes that contain in addition to cold ceramides trace amounts of radiolabeled ceramides. FIG. 13 shows that C18:0-ceramide is adequately taken up by cells, albeit to a lower extent than C16:0-ceramide. Hence the failure of C18:0-ceramide to reverse the MDR phenotype is not due to failure to transfer from liposome into cells but rather is due to intrinsic lack of trafficking capability. These studies confirm that C16:0 ceramide uniquely possesses the capacity to reverse the MDR phenotype.

A second isogenic pair of wild type and MDR cells, the P388 leukemia and a P388 daunorubicin-resistant P-gp overexpressing isolate P388/Dx were studied to assure that the phenotype observed in the ADX cells is generalizable. In this regard, full sphingolipid enzymatic profiling was performed to corroborate that baseline elevation in sphingomyelin/ceramide levels results from increased serine palmitoyl transferase activity. Preliminary evidence described above indicates that daunorubicin-resistant P388 cells display the same baseline sphingolipid abnormalities as ADX cells, and failure to traffic doxorubicin to the nucleus, making this supposition highly likely. In both ADX and P388/Dx cells, reversal of MDR is attempted by inactivating serine palmitoyl transferase by siRNA and pharmacologically using cycloserine as per (7). Preliminary data from his laboratory using liposomes that contain both ceramide and doxorubicin support this strategy.

Lipid Studies: Serine palmitoyl transferase enzymatic activity is measured as in Perry et al. 2000. Serine palmitoyltransferase regulates de novo ceramide generation during etoposide-induced apoptosis. *J Biol Chem* 275:9078-9084. Mass spectrometry of ceramide species is standardized as described in Sullards et al. 2007. Structure-specific, quantitative methods for analysis of sphingolipids by liquid chromatography-tandem mass spectrometry: "inside-out" sphingolipidomics. *Methods Enzymol* 432:83-115.

Interrogation of the Prevalence of Ceramide-daunorubicin Synergy

Cancers that manifest high levels of P-gp, whether spontaneously or therapy-induced, display vesicular trafficking defects and drug resistance, reversible by C16:0 ceramide-based liposomes, whereas cancers that do not overexpress P-gp will traffic drug to the nucleus unhindered.

To demonstrate this, a set of cancer cells in culture that contain high and low P-gp levels based on the literature (10-17), as enumerated in Table 3 are used.

TABLE 3

Drug-induced P-gp overexpressor cells

| Drug Sensitive | Drug Resistant | Origin | Reference |
|---|---|---|---|
| NCI-H460 | NCI-H460/VBL | lung carcinoma | 17 |
| HT29 | HT29 MDR-1 | colon carcinoma cell | 18 |
| HepG2 | HepG2/Dox | hepatocarcinoma | 19 |
| KB-3-1 | KB-V1 | epidemoid carcinoma | 20 |
| MCF7 | MCF7/ADR | breast adenocarcinoma | 21 |

Spontaneous P-gp overexpressor cells

| Drug Resistant | Origin | Reference |
|---|---|---|
| NCI-H295 | adrenocortical carcinoma | 22 |
| A-498 | renal cell carcinoma | 23 |
| ACHN | renal cell carcinoma | 23 |
| HCT-15 | colon carcinoma | 24 |

Confirmation of P-gp status is by real time PCR and Western analysis in accordance with methods known to those of skill in the art. Daunorubicin or doxorubicin is immobilized in vesicles of P-gp high cancer cell lines and traffic to the nucleus in P-gp low cell lines. Further, ceramide-based liposomes induce trafficking of the vesicles to the nucleus in the P-gp high cells reversing chemoresistance. Sphingolipid profiling by mass spectrometry is performed to determine whether altered sphingomyelin or ceramide mass or specific species define the MDR phenotype. Serine palmitoyl transferase enzymatic activity is similarly assessed in P-gp high and low cell types. The ability of C16:0 ceramide liposomes to reverse cross resistance to other MDR drugs such as vincristine and cis-platinum is tested.

P-gp levels are measured by real time PCR as described in Bates et al. 1991. Mitotane enhances cytotoxicity of chemotherapy in cell lines expressing a multidrug resistance gene (mdr-1/P-glycoprotein) which is also expressed by adrenocortical carcinomas. *J Clin Endocrinol Metab* 73:18-29.and confirmed by Western analysis using a murine anti-P-gp Ab that cross reacts with human and mouse P-gp (clone C219; Calbiochem, USA) as described, for example, in Castro et al. 2012. A cytotoxic ribonuclease reduces the expression level of P-glycoprotein in multidrug-resistant cell lines. *Invest New Drugs* 30:880-888.

Reversal of MDR Using Ceramide-containing Nano-liposomes

Figure 15:
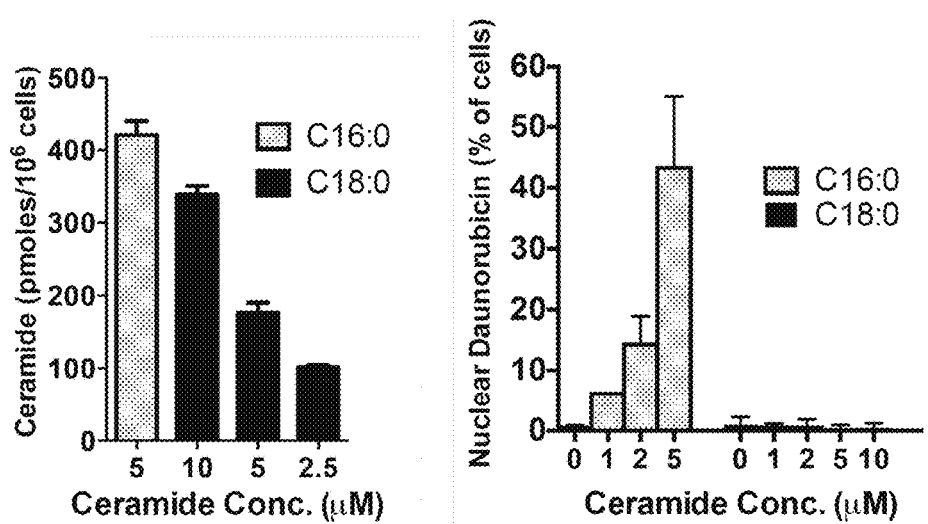
FIG. 15 shows C16:0 ceramide effectiveness in reversing MDR. Left panel: Extent of ceramide transfer from C16:0- or C18:0-ceramide liposomes into ADX cells. These studies used trace $^{14}$C-labeled C16:0- or C18:0-ceramide incorporated into unlabeled ceramide-containing liposomes for quantitation of cellular ceramide uptake. Right panel: Daunorubicin trafficking from MDR vacuoles into the nucleus is independent of extent of ceramide uptake. For these studies, cells were loaded with daunorubicin (20 μM) for 2 hours to isotopic steady state and then treated with 1-5 μM C16:0 or 1-10 μM C18:0 ceramide-containing liposomes. While 5 µM C16:0 ceramide and 10 µM C18:0 ceramide display comparable uptake into ADX cells (left panel), only C16:0 ceramide-based liposomes confer nuclear drug trafficking (right panel).
Figure 17:
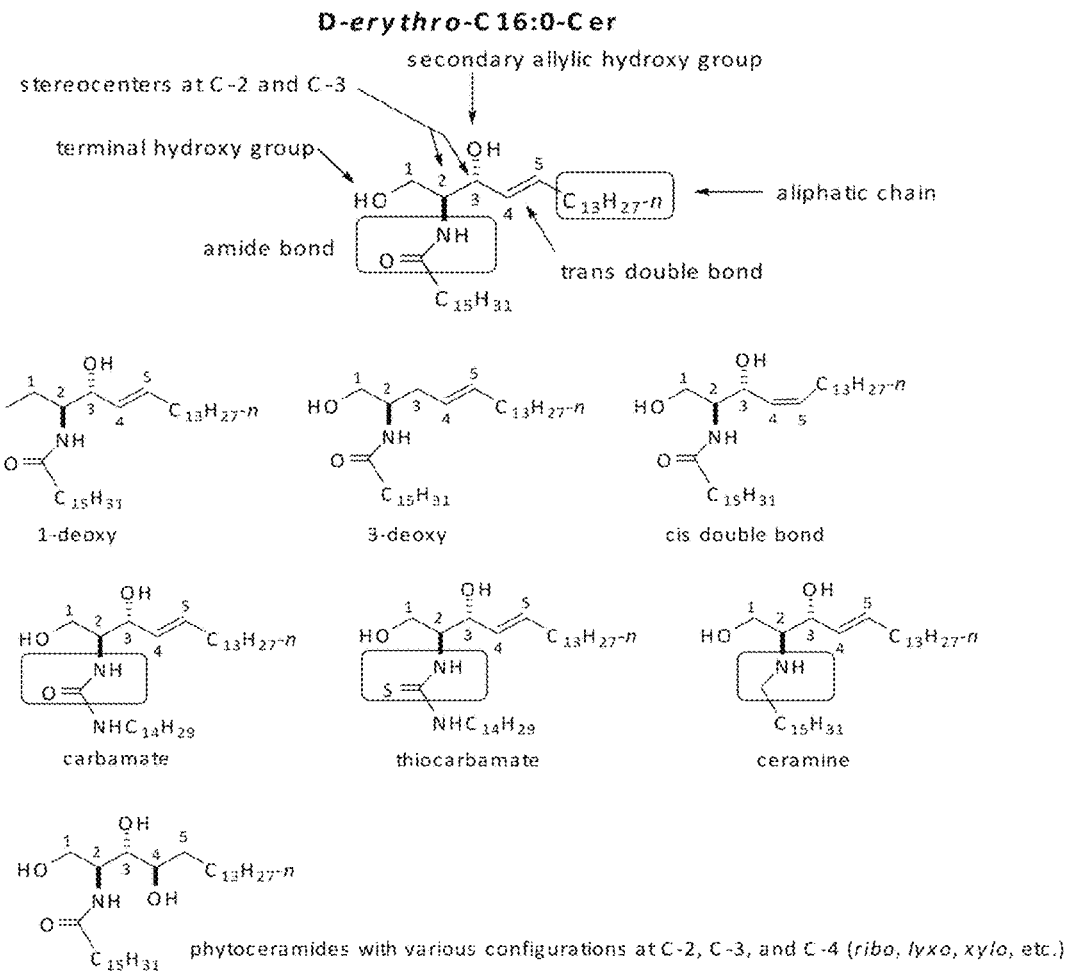
FIG. 17 shows ceramides of various structures.
Figure 18:
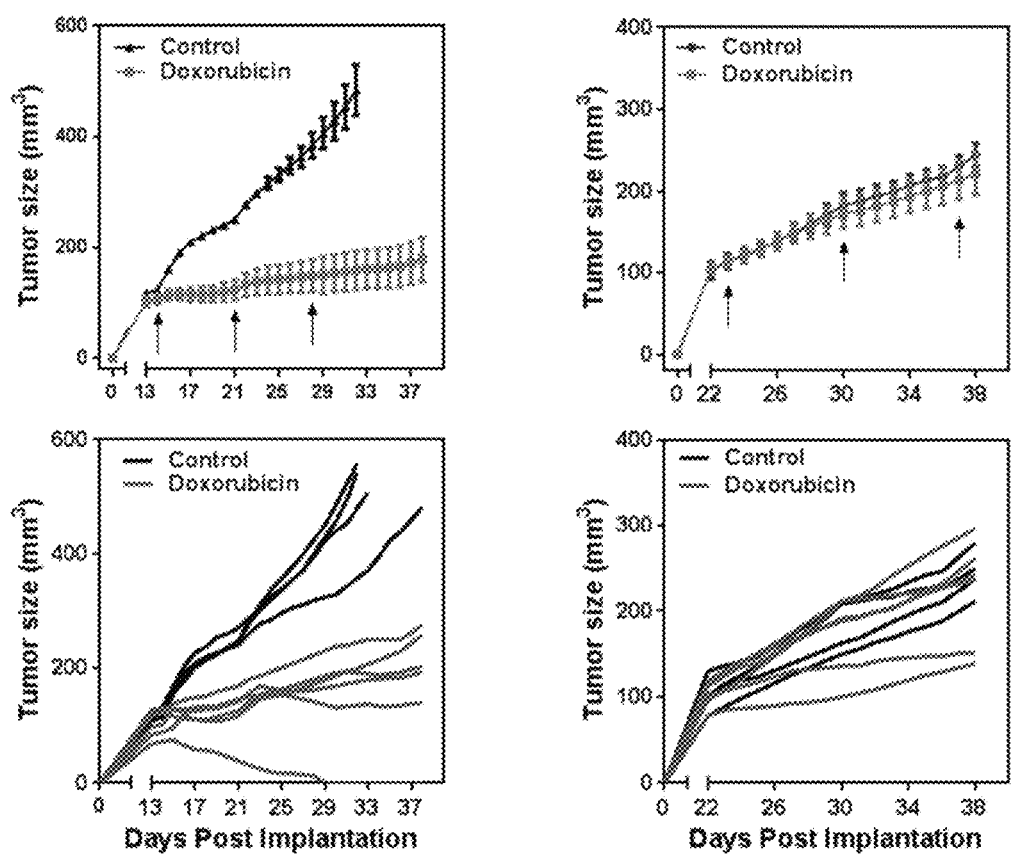
FIG. 18 shows the results of doxorubicin treatment of DC-3F tumor and ADX tumor. Tumors were created in the right flanks of athymic nude mice using $5 \times 10^6$ DC-3F cells or ADX cells and at tumor volumes of 100-150 mm$^3$ were treated with Doxorubicin 8 mg/kg i.v. weekly (arrows) for 3 weeks. Tumor volumes were measured daily according to the formula of Kim et al. (Cancer Res 1986: 46, 1120) for 3 months. Collated data in upper panels represent mean±SEM. Data in lower panels represent individual tumor patterns.

Transfer of ceramide from liposomes into ADX MDR cells was tested using C16:0 ceramide-based liposomes or 018:0 ceramide-based liposomes in order to evaluate whether differences in MDR reversal reflect differences in ceramide delivery or properties unique to C16:0 ceramide structure. For these studies, C16:0 and 018:0 ceramide liposomes were formulated at 10 mol % ceramide containing trace $^{14}$C-labeled C16:0 or $^{14}$C-labeled C18:0 ceramide. ADX cells were incubated with liposomes at 5 µM $^{14}$C-labeled C16:0 or the indicated concentrations of $^{14}$C-labeled C18:0, and after two hours cells were washed and radiolabel incorporation quantified by scintillation counting. ADX cells incubated with 5 µM C16:0 ceramide liposome, a highly effective biologic dose, contained 417±19 pmoles ceramide/$10^6$ cells, whereas at 10 µM C18:0 ceramide, 339±12 pmoles C18:0 ceramide was incorporated/106 cells (FIG. 15, left panel). Despite comparable ceramide uptake, in cells pre-incubated with 20 µM daunorubicin for 2 hours to load the cytoplasmic vesicular compartment to isotopic steady state, nuclear transfer occurred only with C16:0 ceramide treatment (FIG. 1, right panel). These studies indicate that induction of vesicular drug trafficking into the nucleus of MDR cells does not reflect ceramide transfer from liposomes to cells, but rather represents a unique biological effect of the C16:0 ceramide species.

C16:0 Ceramide Confers Daunorubicin-induced Cell Death.

To determine whether restoration of nuclear trafficking of daunorubicin restores chemotherapeutic drug-induced cell death, an MTT cell viability assay was performed in drug resistant ADX cells employing liposomes containing the different ceramide species. C16:0-, C18:0-, 024:0-containing liposomes (at 10 mol % ceramide/liposome) and control liposomes were tested over a range of concentrations for impact on cell viability loss. Only C16:0 ceramide-containing liposomes displayed significant effect on cell viability loss (2-10 µM), while the other liposomes showed no effect except even at the high concentration of 10 µM (FIG. 16). Thus the concentration range for C16:0 ceramide induction of drug trafficking to the nucleus (FIG. 12) is within the same range impacting cell death.

Figure 14:
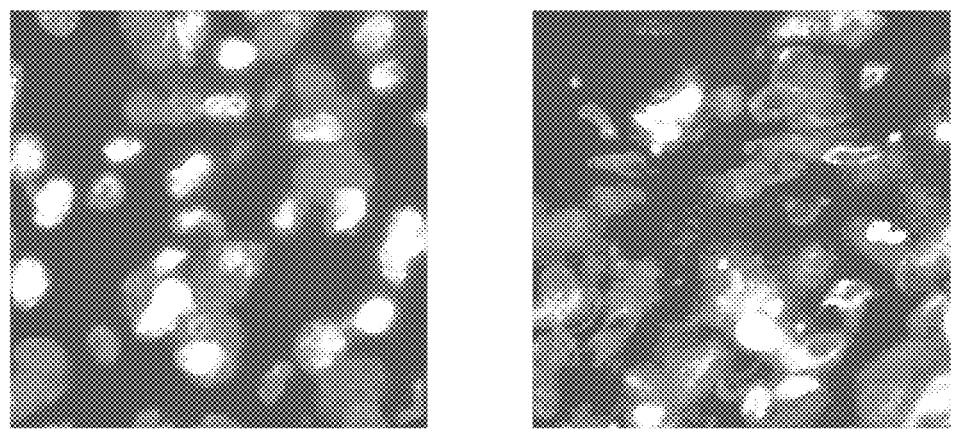
FIG. 14 shows that doxorubicin mislocalization into the cytoplasm of drug-resistant ADX tumors is maintained in vivo. Tumors were excised at 2 hours post doxorubicin injection (24 mg/kg) and cryosectioned. Representative images were obtained using an Axio Widefield Microscope. In the left panel, DC3F tumor cells accumulate drug within the nucleus, whereas in the right panel, MDR ADX tumor cells accumulate drug in the cytoplasmic compartment.

Doxorubicin Localizes to the Cytoplasmic Compartment of ADX Tumors and the Nucleus of DC-3F Tumors Whether the ADX drug resistant cells in vivo would maintain their in vitro phenotype of drug mislocalization to the vesicular compartment was tested. 2.5×$10^6$ ADX or DC-3F parental cells were implanted into the right flank of athymic nude mice. At 100-150 mm3, 24 mg/kg of doxorubicin was injected i.v. into tumor-bearing mice. After 2 hours, tumors were excised and frozen at −80° C. for cryosection. In FIG. 14 (left panel), DC-3F tumors show drug localization to the nucleus while in the right panel, ADX tumors display drug primarily localized to cytoplasm. In preparation for C16:0 ceramide-based reversal of the MDR phenotype in vivo, doxorubicin MTD studies were performed and a dose of 8 mg/kg×3 was defined as the MTD, consistent with the literature in multiple mouse strains. Further, it was shown that parental DC3F tumor is sensitive to this dose of doxorubicin, while the MDR ADX clone is totally resistant to drug (FIG. 14). These data are consistent with the in vitro data and indicate that the characteristics of drug trafficking of these cell lines are maintained in tumors in vivo.

Figure 19:
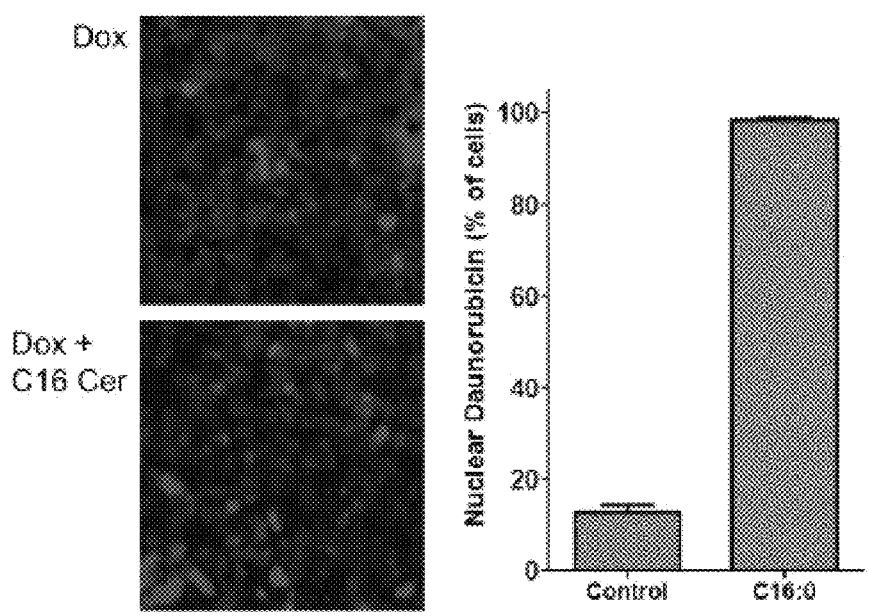
FIG. 19 shows Dox re-distribution in ADX tumor cells after C16:0 ceramide-containing liposomes treatment in vivo. Mice harboring 100 mm$^3$ MDR ADX tumors were treated with 8 mg/kg Dox iv. Left upper panel shows the distribution of Dox in ADX tumor cells at isotopic steady state (1 h). Dox is mostly located in the cytosolic compartment. Left lower panel shows the distribution of Dox after subsequent treatment with 1 µmol/mouse liposomal 16: ceramide. After ceramide treatment, Dox was mostly located in the nucleus of ADX tumor cells. Right panel quantifies this phenomenon.
Figure 20:
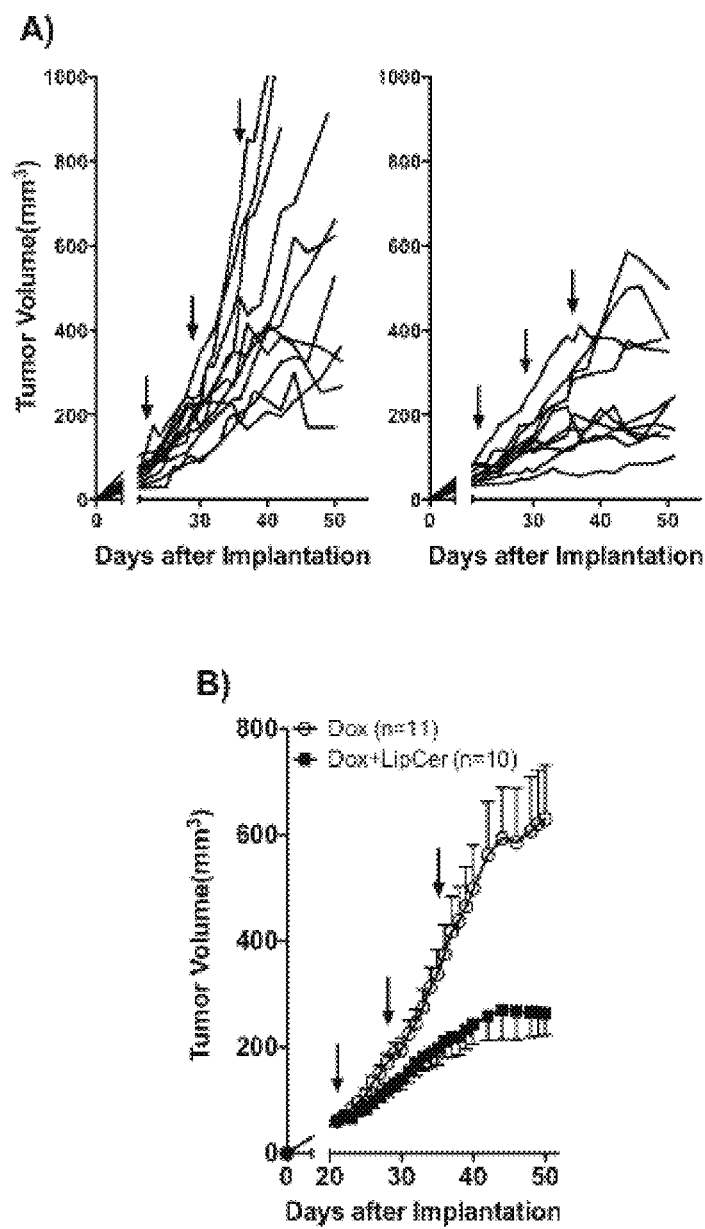
FIG. 20 shows tumor response to Dox and Dox+C16:0 ceramide-containing nano-liposome treatment. Collation of 3 experiments of Dox with or without lipomal ceramide treatment on ADX MDR tumors. $5 \times 10^6$ ADX cells were implanted into athymic nude mice by s.c. injection. Treatment was started on day 21 when tumor was 100 mm$^3$. 8 mg/kg Dox (arrows) was injected i.v. every 7 days followed by 1 µmol/mouse liposomal C16:0 ceramide for a total of 3 treatments (total Dox=24 mg/kg, the MTD in mice). Left panel of A) represents individual tumor growth with Dox alone. Right panel of A) represents tumor response when treated with Dox+1 µmol/mouse liposomal ceramide. Panel B is mean tumor growth response of Dox alone and combined treatment.

C16:0 ceramide-containing nanoliposomes induce Dox trafficking from cytoplasmic vesicles into the nucleus of ADX MDR tumors, chemosensitizing in vivo. ADX flank tumors (in athymic Nude-FoxN1 nu mice) were loaded to isotopic steady state for 1 h by systemic administration of Dox (20 mg/kg), and 1 µmol of C16:0 ceramide containing liposomes/mouse was injected i.v. Mice were sacrificed 1 h thereafter, and tumors snap frozen in OCT at −80° C. As shown in upper left panel of FIG. 19, Dox localized mostly to cytosol of ADX tumor cells. In contrast, Dox localized exclusively to the nucleus of DC-3F parental tumors (not shown). However, after C16:0 ceramide nano-liposome treatment, drug re-localized into the nucleus (lower left panel FIG. 19; quantified in right panel), corresponding closely to the in vitro data. Complementary tumor response data (FIG. 20) show significant chemosensitization upon C16:0 nano-liposome treatment (p<0.001). Note liposomes without ceramide were ineffective (not shown). These studies serve as the basis for Aim 3 that attempts to provide pre-clinical data supporting development of a C16:0 ceramide Doxil-like particle for clinical use in MDR tumors.

Methods: Liposome Delivery, MTD, PK: Liposomes and free doxorubicin are delivered intravenously and MTD and PK determined in accordance with known protocols. (For example, see Barenholz et al. 2012. *J Control Release* 160:117-134 and Pramanik et al. 2012. *Oncotarget* 3:640-650).

DC-3F/ADX tumors: DC-3F/ADX cells ($2.5 \times 10^6$) are injected subcutaneously into the flank of 5-6 week old male Swiss nude mice (Charles River) in a 1:1 dilution with BD matrigel (BD Biosciences) final volume 200 µl. Tumors reach approximately 1 cm at 5-6 weeks, and are dissected into warm PBS, cut into 25-50 mg cubes, and implanted in anesthetized mice subcutaneously. At 10 days to 2 weeks after implantation when tumors reach 200 mm$^3$, they will be randomly divided into experimental groups (5-10 mice/group), treated with 1.5-2.3 mg/kg free doxorubicin, and after doxorubicin steady state in tumor cells has been reached (to be determined empirically), treated with C16:0 ceramide-based liposomes. Tumors will be excised for confocal fluorescence at varying times thereafter from 30 min to 24 h as per (19), or followed for tumor response by standard caliper measurement. In subsequent studies, up to 4 doses of doxorubicin will be delivered (published MTD about 9 mg/kg×4 doses/25 g mouse) with or without C16:0-based liposomes accompanying each dose of doxorubicin).

CONCLUSION

Vesicular transport of drugs to nuclear targets is a poorly studied area. The MDR phenotype, which appears to disrupt this process allows for visualization of this unique compartment that contains drug frozen in time and space. Identification of this compartment found defective in P-gp overexpressing cells dependent on a unique sphingolipid C16:0 ceramide for carrying out its function represents a scientific discovery. In addition to its potential importance in drug trafficking in the P-gp MDR phenotype, the discovery that a single natural ceramide species confers vesicular transport properties has substantive implication for the field of sphingolipid signaling. Hence, identification of this vesicular compartment and the role of C16:0 ceramide in its function is in of itself worthy of scientific attention. The translational significance of the discovery of sphingolipid regulation of this compartment has clinical potential.

REFERENCES

1. Mesicek, J., Lee, H., Feldman, T., Jiang, X., Skobeleva, A., Berdyshev, E. V., Haimovitz-Friedman, A., Fuks, Z., and Kolesnick, R. 2010. Ceramide synthases 2, 5 and 6 confer distinct roles in radiation-induced apoptosis in HeLa cells. *Cell Signal* 22:1300-1307.

2. Barenholz, Y. 2012. Doxil®—the first FDA-approved nano-drug: lessons learned. *J Control Release* 160:117-134.

3. Khazanov, E., Priev, A., Shillemans, J. P., and Barenholz, Y. 2008. Physicochemical and biological characterization of ceramide-containing liposomes: paving the way to ceramide therapeutic application. *Langmuir* 24:6965-6980.

4. Chen, K. G., and Sikic, B. I. 2012. Molecular pathways: regulation and therapeutic implications of multidrug resistance. *Clin Cancer Res* 18:1863-1869.

5. Lee, H., Rotolo, J. A., Mesicek, J., Penate-Medina, T., Rimner, A., Liao, W. C., Yin, X., Ragupathi, G., Ehleiter, D., Gulbins, E., et al. 2011. Mitochondrial Ceramide-Rich Macrodomains Functionalize Bax upon Irradiation. *PLoS ONE* 6:e19783.

6. Stancevic, B. 2010. Ceramide-Rich Platforms Regulate Ionizing Radiation Sensitivity in Endothelium. In *Pharmacology*. New York: Weill Cornell Graduate School of Medical Sciences 142.

7. Lowther, J., Naismith, J. H., Dunn, T. M., and Campopiano, D. J. 2012. Structural, mechanistic and regulatory studies of serine palmitoyltransferase. *Biochem Soc Trans* 40:547-554.

8. Perry, D. K., Carton, J., Shah, A. K., Meredith, F., Uhlinger, D. J., and Hannun, Y. A. 2000. Serine palmitoyltransferase regulates de novo ceramide generation during etoposide-induced apoptosis. *J Biol Chem* 275:9078-9084.

9. Sullards, M. C., Allegood, J. C., Kelly, S., Wang, E., Haynes, C. A., Park, H., Chen, Y., and Merrill, A. H. J. 2007. Structure-specific, quantitative methods for analysis of sphingolipids by liquid chromatography-tandem mass spectrometry: "inside-out" sphingolipidomics. *Methods Enzymol* 432:83-115.

10. Caceres, G., Robey, R. W., Sokol, L., McGraw, K. L., Clark, J., Lawrence, N. J., Sebti, S. M., Wiese, M., and List, A. F. 2012. HG-829 Is a Potent Noncompetitive Inhibitor of the ATP-Binding Cassette Multidrug Resistance Transporter ABCB1. *Cancer Res* 72:4204-4213.

11. Schumacher, U., Nehmann, N., Adam, E., Mukthar, D., Slotki, I. N., Horny, H. P., Flens, M. J., Schlegelberger, B., and Steinemann, D. 2012. MDR-1-overexpression in HT 29 colon cancer cells grown in SCID mice. *Acta Histochem* 114:594-602.

12. Hu, Y. J., Shen, X. L., Lu, H. L., Zhang, Y. H., Huang, X. A., Fu, L. C., and Fong, W. F. 2008. Tenacigenin B derivatives reverse P-glycoprotein-mediated multidrug resistance inHepG2/Dox cells. *J Nat Prod* 71:1049-1051.

13. Limtrakul, P., Khantamat, O., and Pintha, K. 2004. Inhibition of P-glycoprotein activity and reversal of cancer multidrug resistance by Momordica charantia extract. *Cancer Chemother Pharmacol* 54:525-530.

14. He, S., Liu, F., Xie, Z., Zu, X., Xu, W., and Jiang, Y. 2010. P-Glycoprotein/MDR1 Regulates Pokemon Gene Transcription Through p53 Expression in Human Breast Cancer Cells. *Int J Mol Sci* 11:3309-3051.

15. Bates, S. E., Shieh, C. Y., Mickley, L. A., Dichek, H. L., Gazdar, A., Loriaux, D. L., and Fojo, A. T. 1991. Mitotane enhances cytotoxicity of chemotherapy in cell lines expressing a multidrug resistance gene (mdr-1/P-glycoprotein) which is also expressed by adrenocortical carcinomas. *J Clin Endocrinol Metab* 73:18-29.

16. Keller, G., Schally, A. V., Nagy, A., Halmos, G., Baker, B., and Engel, J. B. 2005. Targeted chemotherapy with cytotoxic bombesin analogue AN-215 can overcome chemoresistance in experimental renal cell carcinomas. *Cancer* 104:2266-2274.

17. Guichard, S. M., Macpherson, J. S., Thurston, D. E., and Jodrell, D. I. 2005. Influence of P-glycoprotein expression on in vitro cytotoxicity and in vivo antitumour activity of the novel pyrrolobenzodiazepine dimer SJG-136. *Eur J Cancer* 41:1811-1818.

18. Castro, J., Ribó M., Puig, T., Colomer, R., Vilanova, M., and Benito, A. 2012. A cytotoxic ribonuclease reduces the expression level of P-glycoprotein in multidrug-resistant cell lines. *Invest New Drugs* 30:880-888.

19. Pramanik, D., Campbell, N. R., Das, S., Gupta, S., Chenna, V., Bisht, S., Sysa-Shah, P., Bedja, D., Karikari, C., Steenbergen, C., et al. 2012. A composite polymer nanoparticle overcomes multidrug resistance and ameliorates doxorubicin-associated cardiomyopathy. *Oncotarget* 3:640-650.

20. Barth, B. M., Cabot, M. C., and Kester, M. 2011. Ceramide-based therapeutics for the treatment of cancer. *Anticancer Agents Med Chem* 11:911-919.

What is claimed:

1. A method for inducing nuclear trafficking of a therapeutic agent and reversing multi-drug resistance (MDR) in cancer cells that overexpress P-glycoprotein (P-gp) comprising contacting said cancer cells with the therapeutic agent and C16-ceramide.

2. The method of claim 1, wherein said cancer cells are contacted with a nano-liposome comprising said C16-ceramide.

3. The method of claim 1, wherein said therapeutic agent is an anti-cancer therapeutic agent.

4. The method of claim 1, wherein said cancer cells are contacted with C16:0 prior to, simultaneously with, or after exposure of said tumor cells to the therapeutic agent.

5. A method for treating a P-gp-mediated MDR cancer, the method comprising administering to a subject in need thereof, a therapeutically effective amount of C16:0-ceramide.

6. The method of claim 5, wherein the C16:0 ceramide is administered as part of a nano-liposome.

7. A nano-liposome comprising a C16-ceramide, wherein said nano-liposome induces nuclear trafficking of a therapeutic agent when applied to a cell that overexpresses P-glycoprotein (P-gp) lipid transporter and exhibits multi-drug resistance (MDR).

8. The nano-liposome of claim 7, wherein said ceramide is present in an amount between 1% to 75% of said total lipid composition of said liposome.

9. The nano-liposome of claim 7, wherein said ceramide is present in an amount between 5% to 50% of said total lipid composition of said liposome.

10. The nano-liposome of claim 7, wherein said ceramide is present in an amount between 10% to 25% of said total lipid composition of said liposome.

11. The nano-liposome of claim 7, wherein said nano-liposome consists essentially of fully hydrogenated soybean phosphatidylcholine (HSPC), N-carbamyl-poly-(ethylene glycol methyl ether)-1,2-distearoyl-sn-glyco-3-phosphoethanolamine (2kPEG-DSPE), and ceramide in a mol/mol ratio of 82.5:7.5:10.

12. The nano-liposome of claim 7, wherein said nano-liposome has a mean diameter of about 50 nM to about 200 nM.

13. The nano-liposome of claim 7, wherein said nano-liposome has a mean diameter of about 75 nM to about 150 nM.

14. The nano-liposome of claim 7, wherein said nano-liposome has a mean diameter of about 90 nM to about 125 nM in size.

15. The nano-liposome of claim 7, wherein said nano-liposome further comprises a therapeutic agent.

16. The nano-liposome of claim 15, wherein said therapeutic agent is selected from the group consisting of doxorubicin, daunorubicin, vincristine, cisplatin.

17. A method for selective treatment of a cancer associated with high lipid transporter P-glycoprotein (P-gp) levels, the method comprising administering to a subject in need thereof a ceramide-based nano-liposome of claim 7.

18. A pharmaceutical composition comprising a nano-liposome of any of claims 7 and a pharmaceutically acceptable carrier.

19. A method for the selection of appropriate treatment for a subject with a MDR cancer, the method comprising:
   (a) determining the levels of lipid transporter P-glycoprotein (P-gp) in a tumor cell from the subject;
   (b) identifying the tumor as MDR if levels of lipid transporter P-glycoprotein (P-gp) in a cell from said tumor are elevated in comparison to levels from a cell that is drug sensitive.
   (c) administering exogenous ceramide with an anti-cancer agent if the tumor is identified as MDR.

* * * * *